United States Patent
Knowlton et al.

(10) Patent No.: US 7,006,874 B2
(45) Date of Patent: Feb. 28, 2006

(54) TREATMENT APPARATUS WITH ELECTROMAGNETIC ENERGY DELIVERY DEVICE AND NON-VOLATILE MEMORY

(75) Inventors: Edward W. Knowlton, Danville, CA (US); Bryan Weber, Livermore, CA (US); Mitchell Levinson, Pleasanton, CA (US)

(73) Assignee: Thermage, Inc., Hayward, CA (US)

( * ) Notice: Subject to any disclaimer, the term of this patent is extended or adjusted under 35 U.S.C. 154(b) by 175 days.

(21) Appl. No.: 10/404,250

(22) Filed: Mar. 31, 2003

(65) Prior Publication Data

US 2004/0002704 A1   Jan. 1, 2004

Related U.S. Application Data

(63) Continuation-in-part of application No. 10/400,187, filed on Mar. 25, 2003, which is a continuation-in-part of application No. 10/072,475, filed on Feb. 6, 2002, and a continuation-in-part of application No. 10/072,610, filed on Feb. 6, 2002, which is a continuation-in-part of application No. 09/522,275, filed on Mar. 9, 2000, now Pat. No. 6,413,255, application No. 10/404,250, and a continuation-in-part of application No. 10/026,870, filed on Dec. 20, 2001, now Pat. No. 6,749,624, which is a continuation of application No. 09/337,015, filed on Jun. 30, 1999, now Pat. No. 6,350,276, which is a continuation-in-part of application No. 08/583,815, filed on Jan. 5, 1996, now Pat. No. 6,241,753, and a continuation-in-part of application No. 08/827,237, filed on Mar. 28, 1997, now Pat. No. 6,430,446, and a continuation-in-part of application No. 08/914,681, filed on Aug. 19, 1997, now Pat. No. 5,919,219, and a continuation-in-part of application No. 08/942,274, filed on Sep. 30, 1997, now Pat. No. 6,425,912.

(51) Int. Cl.
*A61F 2/00* (2006.01)

(52) U.S. Cl. .................. 607/101; 607/102; 607/104

(58) Field of Classification Search ............. 607/96, 607/98, 99, 101–102, 104; 606/1, 9
See application file for complete search history.

(56) References Cited

U.S. PATENT DOCUMENTS 3,831,604 A   8/1974   Neefe (Continued)

FOREIGN PATENT DOCUMENTS

DE   1 949 534   4/1970

(Continued)

OTHER PUBLICATIONS

Thermage, Inc., "Complaint For Patent Infringement", Jul. 23, 2004.

(Continued)

*Primary Examiner*—Roy D. Gibson
(74) *Attorney, Agent, or Firm*—Wood, Herron & Evans, L.L.P.

(57) ABSTRACT

An apparatus for cooling a skin surface includes a support structure coupled to an electromagnetic energy delivery device. The electromagnetic energy delivery device is configured to be coupled to an electromagnetic energy source. A cooling member is coupled to the electromagnetic energy delivery device and is configured to create a reverse thermal gradient through a skin surface. A memory is coupled to the electromagnetic energy delivery device and is positioned at the support structure or the electromagnetic energy delivery device. The memory is configured to store information to facilitate operation of at least one of the cooling member, and the electromagnetic energy source. Resources are coupled to the cooling member to permit different levels of cooling at different times of treatment.

26 Claims, 15 Drawing Sheets

U.S. PATENT DOCUMENTS

| | | | |
|---|---|---|---|
| 4,074,718 A | 2/1978 | Morrison |
| 4,140,130 A | 2/1979 | Storm, III |
| 4,164,226 A | 8/1979 | Tapper |
| 4,290,435 A | 9/1981 | Waggott |
| 4,343,301 A | 8/1982 | Indech |
| 4,346,715 A | 8/1982 | Gammell |
| 4,375,220 A | 3/1983 | Matvias |
| 4,381,007 A | 4/1983 | Doss |
| 4,441,486 A | 4/1984 | Pounds |
| 4,545,368 A | 10/1985 | Rand et al. |
| 4,556,070 A | 12/1985 | Vaguine et al. |
| 4,585,237 A | 4/1986 | Koop |
| 4,633,875 A | 1/1987 | Turner |
| 4,646,737 A | 3/1987 | Hussein et al. |
| 4,676,258 A | 6/1987 | Inokuchi et al. |
| 4,709,372 A | 11/1987 | Rando et al. |
| 4,709,701 A | 12/1987 | Weber |
| 4,756,310 A | 7/1988 | Bitterly |
| RE32,849 E | 1/1989 | Wei et al. |
| 4,864,098 A | 9/1989 | Basanese et al. |
| 4,881,543 A | 11/1989 | Trembly et al. |
| 4,887,614 A | 12/1989 | Shirakami et al. |
| 4,889,122 A | 12/1989 | Watmough et al. |
| 4,891,820 A | 1/1990 | Rando et al. |
| 4,944,302 A | 7/1990 | Hernandez et al. |
| 4,957,480 A | 9/1990 | Morenings |
| 4,962,761 A | 10/1990 | Golden |
| 4,976,709 A | 12/1990 | Sand |
| 5,003,991 A | 4/1991 | Takayama et al. |
| 5,011,483 A | 4/1991 | Sleister |
| 5,057,104 A | 10/1991 | Chess |
| 5,100,402 A | 3/1992 | Fan |
| 5,107,832 A | 4/1992 | Guibert et al. |
| 5,131,904 A | 7/1992 | Markoll |
| 5,133,351 A | 7/1992 | Masaki |
| 5,136,676 A | 8/1992 | Arnett et al. |
| 5,143,063 A | 9/1992 | Fellner |
| 5,186,181 A | 2/1993 | Franconi et al. |
| 5,190,031 A | 3/1993 | Guibert et al. |
| 5,190,517 A | 3/1993 | Zieve et al. |
| 5,217,455 A | 6/1993 | Tan |
| 5,230,334 A | 7/1993 | Klopotek |
| 5,231,997 A | 8/1993 | Kikuchi et al. |
| 5,249,192 A | 9/1993 | Kuizenga et al. |
| 5,249,575 A | 10/1993 | DiMino et al. |
| 5,282,797 A | 2/1994 | Chess |
| 5,290,273 A | 3/1994 | Tan |
| 5,300,097 A | 4/1994 | Lerner et al. |
| 5,304,169 A | 4/1994 | Sand |
| 5,304,171 A | 4/1994 | Gregory et al. |
| 5,312,395 A | 5/1994 | Tan et al. |
| 5,315,994 A | 5/1994 | Guibert et al. |
| 5,334,193 A | 8/1994 | Nardella |
| 5,342,357 A | 8/1994 | Nardella |
| 5,344,418 A | 9/1994 | Ghaffari |
| 5,348,554 A | 9/1994 | Imran et al. |
| 5,360,447 A | 11/1994 | Koop |
| 5,364,394 A | 11/1994 | Mehl |
| 5,366,443 A | 11/1994 | Eggers et al. |
| 5,370,642 A | 12/1994 | Keller |
| 5,374,265 A | 12/1994 | Sand |
| 5,387,176 A | 2/1995 | Markoll |
| 5,397,327 A | 3/1995 | Koop et al. |
| 5,401,272 A | 3/1995 | Perkins |
| 5,405,368 A | 4/1995 | Eckhouse |
| 5,423,807 A | 6/1995 | Milder |
| 5,423,811 A | 6/1995 | Imran et al. |
| 5,437,662 A | 8/1995 | Nardella |
| 5,454,808 A | 10/1995 | Koop et al. |
| 5,456,260 A | 10/1995 | Kollias et al. |
| 5,458,596 A | 10/1995 | Lax et al. |
| 5,462,521 A | 10/1995 | Brucker et al. |
| 5,464,436 A | 11/1995 | Smith |
| 5,486,172 A | 1/1996 | Chess |
| 5,496,312 A | 3/1996 | Klicek |
| 5,496,314 A | 3/1996 | Eggers et al. |
| 5,500,012 A | 3/1996 | Brucker et al. |
| 5,507,790 A | 4/1996 | Weiss |
| 5,509,916 A | 4/1996 | Taylor |
| 5,522,813 A | 6/1996 | Trelles |
| 5,522,814 A | 6/1996 | Bernaz |
| 5,527,308 A | 6/1996 | Anderson et al. |
| 5,527,350 A | 6/1996 | Grove et al. |
| 5,531,739 A | 7/1996 | Trelles |
| 5,556,377 A | 9/1996 | Rosen et al. |
| 5,556,612 A | 9/1996 | Anderson et al. |
| 5,558,667 A | 9/1996 | Yarborough et al. |
| 5,569,242 A | 10/1996 | Lax et al. |
| 5,571,216 A | 11/1996 | Anderson |
| 5,578,029 A | 11/1996 | Trelles et al. |
| 5,595,568 A | 1/1997 | Anderson et al. |
| 5,599,342 A | 2/1997 | Hsia et al. |
| 5,620,478 A | 4/1997 | Eckhouse |
| 5,626,631 A | 5/1997 | Eckhouse |
| 5,628,744 A | 5/1997 | Coleman et al. |
| 5,643,334 A | 7/1997 | Eckhouse et al. |
| 5,649,923 A | 7/1997 | Gregory et al. |
| 5,655,547 A | 8/1997 | Karni |
| 5,660,836 A | 8/1997 | Knowlton |
| 5,669,868 A | 9/1997 | Markoll |
| 5,681,282 A | 10/1997 | Eggers et al. |
| 5,683,366 A | 11/1997 | Eggers et al. |
| 5,683,380 A | 11/1997 | Eckhouse et al. |
| 5,692,058 A | 11/1997 | Eggers et al. |
| 5,693,045 A | 12/1997 | Eggers |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,720,772 A | 2/1998 | Eckhouse |
| 5,730,719 A | 3/1998 | Edwards |
| 5,735,844 A | 4/1998 | Anderson et al. |
| 5,743,901 A | 4/1998 | Grove et al. |
| 5,746,735 A | 5/1998 | Furumoto et al. |
| 5,749,868 A | 5/1998 | Furumoto |
| 5,754,573 A | 5/1998 | Yarborough et al. |
| 5,755,751 A | 5/1998 | Eckhouse |
| 5,755,753 A | 5/1998 | Knowlton |
| 5,769,879 A | 6/1998 | Richards et al. |
| 5,775,338 A | 7/1998 | Hastings |
| 5,776,092 A | 7/1998 | Farin et al. |
| 5,776,175 A | 7/1998 | Eckhouse et al. |
| 5,810,801 A | 9/1998 | Anderson et al. |
| 5,814,008 A | 9/1998 | Chen et al. |
| 5,814,040 A | 9/1998 | Nelson et al. |
| 5,814,041 A | 9/1998 | Anderson et al. |
| 5,820,626 A | 10/1998 | Baumgardner |
| 5,833,612 A | 11/1998 | Eckhouse et al. |
| 5,836,999 A | 11/1998 | Eckhouse et al. |
| 5,843,072 A | 12/1998 | Furumoto et al. |
| 5,843,078 A | 12/1998 | Sharkey |
| 5,849,029 A | 12/1998 | Eckhouse et al. |
| 5,851,181 A | 12/1998 | Talmor |
| 5,871,479 A | 2/1999 | Furumoto et al. |
| 5,879,326 A | 3/1999 | Godshall et al. |
| 5,879,346 A | 3/1999 | Waldman et al. |
| 5,880,880 A | 3/1999 | Anderson et al. |
| 5,885,273 A | 3/1999 | Eckhouse et al. |
| 5,885,274 A | 3/1999 | Fullmer et al. |
| 5,906,609 A | 5/1999 | Assa et al. |
| 5,911,718 A | 6/1999 | Yarborough et al. |
| 5,925,078 A | 7/1999 | Anderson |
| 5,938,657 A | 8/1999 | Assa et al. |
| 5,948,009 A | 9/1999 | Tu |

| Patent No. | Date | Inventor |
|---|---|---|
| 5,964,749 A | 10/1999 | Eckhouse et al. |
| 5,968,034 A | 10/1999 | Fullmer et al. |
| 5,970,983 A | 10/1999 | Karni et al. |
| 5,976,123 A * | 11/1999 | Baumgardner et al. ....... 606/13 |
| 5,976,128 A * | 11/1999 | Schilling et al. .............. 606/34 |
| 5,979,454 A | 11/1999 | Anvari et al. |
| 5,983,900 A | 11/1999 | Clement et al. |
| 5,995,283 A | 11/1999 | Anderson et al. |
| 5,997,530 A | 12/1999 | Nelson et al. |
| 6,014,579 A | 1/2000 | Pomeranz et al. |
| 6,015,404 A | 1/2000 | Altshuler et al. |
| 6,027,495 A | 2/2000 | Miller |
| RE36,634 E | 3/2000 | Ghaffari |
| 6,045,548 A | 4/2000 | Furumoto et al. |
| 6,047,215 A | 4/2000 | McClure et al. |
| 6,050,990 A | 4/2000 | Tankovich et al. |
| 6,053,909 A | 4/2000 | Shadduck |
| 6,066,130 A | 5/2000 | Gregory et al. |
| 6,077,294 A | 6/2000 | Cho et al. |
| 6,081,749 A | 6/2000 | Ingle et al. |
| 6,090,101 A | 7/2000 | Quon et al. |
| 6,104,959 A | 8/2000 | Spertell |
| 6,120,497 A | 9/2000 | Anderson et al. |
| 6,126,655 A | 10/2000 | Domankevitz et al. |
| 6,129,723 A | 10/2000 | Anderson et al. |
| 6,139,569 A | 10/2000 | Ingle et al. |
| 6,139,653 A | 10/2000 | Fernandes et al. |
| 6,147,503 A | 11/2000 | Nelson et al. |
| 6,159,194 A | 12/2000 | Eggers et al. |
| 6,162,212 A | 12/2000 | Kreindel et al. |
| 6,168,590 B1 | 1/2001 | Neev |
| 6,171,301 B1 | 1/2001 | Nelson et al. |
| 6,183,773 B1 | 2/2001 | Anderson |
| 6,187,001 B1 | 2/2001 | Azar et al. |
| 6,200,308 B1 | 3/2001 | Pope et al. |
| 6,210,402 B1 | 4/2001 | Olsen et al. |
| 6,214,034 B1 | 4/2001 | Azar |
| 6,228,075 B1 | 5/2001 | Furumoto |
| 6,235,024 B1 | 5/2001 | Tu |
| 6,240,925 B1 | 6/2001 | McMillan et al. |
| 6,248,103 B1 | 6/2001 | Tannenbaum et al. |
| 6,254,594 B1 | 7/2001 | Berry |
| 6,267,758 B1 | 7/2001 | Daw et al. |
| 6,273,883 B1 | 8/2001 | Furumoto |
| 6,273,884 B1 | 8/2001 | Altshuler et al. |
| 6,273,885 B1 | 8/2001 | Koop et al. |
| 6,275,962 B1 | 8/2001 | Fuller et al. |
| 6,280,438 B1 | 8/2001 | Eckhouse et al. |
| 6,283,956 B1 | 9/2001 | McDaniel |
| 6,299,620 B1 | 10/2001 | Shadduck et al. |
| 6,334,074 B1 | 12/2001 | Spertell |
| 6,336,926 B1 | 1/2002 | Goble |
| 6,337,998 B1 | 1/2002 | Behl et al. |
| 6,350,261 B1 | 2/2002 | Domankevitz et al. |
| 6,383,176 B1 | 5/2002 | Connors et al. |
| 6,387,089 B1 | 5/2002 | Kreindel et al. |
| 6,387,103 B1 | 5/2002 | Shadduck |
| 6,402,739 B1 | 6/2002 | Neev |
| 6,408,212 B1 | 6/2002 | Neev |
| 6,409,722 B1 * | 6/2002 | Hoey et al. .................... 606/34 |
| 6,413,253 B1 | 7/2002 | Koop et al. |
| 6,413,255 B1 | 7/2002 | Stern |
| 6,436,094 B1 | 8/2002 | Reuter |
| 6,451,007 B1 | 9/2002 | Koop et al. |
| 6,463,336 B1 | 10/2002 | Mawhinney |
| 6,485,484 B1 | 11/2002 | Connors et al. |
| 6,488,696 B1 | 12/2002 | Cho et al. |
| 6,500,141 B1 | 12/2002 | Irion et al. |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,514,244 B1 | 2/2003 | Pope et al. |
| 6,527,763 B1 | 3/2003 | Esch et al. |
| 6,529,543 B1 | 3/2003 | Anderson et al. |
| 6,533,775 B1 | 3/2003 | Rizoiu |
| 6,537,272 B1 * | 3/2003 | Christopherson et al. ..... 606/34 |
| 6,569,155 B1 | 5/2003 | Connors et al. |
| 6,600,951 B1 | 7/2003 | Anderson |
| 6,605,079 B1 | 8/2003 | Tucek et al. |
| 6,605,080 B1 | 8/2003 | Altshuler et al. |
| 6,623,454 B1 | 9/2003 | Eggers et al. |
| 6,629,974 B1 | 10/2003 | Penny et al. |
| 6,632,218 B1 | 10/2003 | Furumoto et al. |
| 6,649,904 B1 | 11/2003 | Hayashi et al. |
| 6,653,618 B1 | 11/2003 | Zenzie |
| 6,659,999 B1 | 12/2003 | Anderson et al. |
| 6,662,054 B1 | 12/2003 | Kreindel et al. |
| 6,666,856 B1 | 12/2003 | Connors et al. |
| 6,702,808 B1 | 3/2004 | Kreindel |
| 6,702,838 B1 | 3/2004 | Andersen et al. |
| 6,706,032 B1 | 3/2004 | Weaver et al. |
| 6,723,090 B1 | 4/2004 | Altshuler et al. |
| 6,743,222 B1 | 6/2004 | Durkin et al. |
| 6,749,602 B1 | 6/2004 | Sierra et al. |
| 6,758,845 B1 | 7/2004 | Weckwerth et al. |
| 2001/0037118 A1 | 11/2001 | Shadduck |
| 2002/0016587 A1 | 2/2002 | Furumoto |
| 2002/0016601 A1 | 2/2002 | Shadduck |
| 2002/0019625 A1 | 2/2002 | Azar |
| 2002/0022827 A1 | 2/2002 | Esch et al. |
| 2002/0035360 A1 | 3/2002 | Conners et al. |
| 2002/0049433 A1 | 4/2002 | Furumoto et al. |
| 2002/0065533 A1 | 5/2002 | Weaver et al. |
| 2002/0091377 A1 | 7/2002 | Anderson et al. |
| 2002/0111605 A1 | 8/2002 | Furumoto et al. |
| 2002/0123743 A1 | 9/2002 | Shanks, et al. |
| 2002/0123745 A1 | 9/2002 | Svaasand et al. |
| 2002/0151887 A1 | 10/2002 | Stern et al. |
| 2002/0156471 A1 | 10/2002 | Stern et al. |
| 2002/0161357 A1 | 10/2002 | Anderson et al. |
| 2002/0161362 A1 | 10/2002 | Penny et al. |
| 2002/0183724 A1 | 12/2002 | Neev |
| 2002/0183789 A1 | 12/2002 | Neev |
| 2003/0023283 A1 | 1/2003 | McDaniel |
| 2003/0028186 A1 | 2/2003 | Kreindel |
| 2003/0032950 A1 | 2/2003 | Altshuler et al. |
| 2003/0036751 A1 | 2/2003 | Anderson et al. |
| 2003/0040739 A1 | 2/2003 | Koop |
| 2003/0055414 A1 | 3/2003 | Altshuler et al. |
| 2003/0059386 A1 | 3/2003 | Sumian et al. |
| 2003/0065313 A1 | 4/2003 | Koop et al. |
| 2003/0065314 A1 | 4/2003 | Altshuler et al. |
| 2003/0069567 A1 | 4/2003 | Eckhouse et al. |
| 2003/0097162 A1 | 5/2003 | Kreindel |
| 2003/0129154 A1 | 7/2003 | McDaniel |
| 2003/0130710 A1 | 7/2003 | Baker et al. |
| 2003/0139740 A1 | 7/2003 | Kreindel |
| 2003/0163178 A1 | 8/2003 | Davison et al. |
| 2003/0187488 A1 | 10/2003 | Kreindel et al. |
| 2003/0199859 A1 | 10/2003 | Altshuler et al. |
| 2003/0208326 A1 | 11/2003 | Chen et al. |
| 2003/0218756 A1 | 11/2003 | Chen et al. |
| 2003/0220749 A1 | 11/2003 | Chen et al. |
| 2003/0233138 A1 | 12/2003 | Spooner |
| 2003/0236487 A1 | 12/2003 | Knowlton |
| 2004/0015157 A1 | 1/2004 | Connors et al. |
| 2004/0034319 A1 | 2/2004 | Anderson et al. |
| 2004/0034341 A1 | 2/2004 | Altshuler et al. |
| 2004/0039379 A1 | 2/2004 | Viator et al. |
| 2004/0093042 A1 | 5/2004 | Altshuler et al. |
| 2004/0133251 A1 | 7/2004 | Altshuler et al. |
| 2004/0147984 A1 | 7/2004 | Altshuler et al. |
| 2004/0162549 A1 | 8/2004 | Altshuler |
| 2004/0199226 A1 | 10/2004 | Shadduck |

FOREIGN PATENT DOCUMENTS

| | | |
|---|---|---|
| DE | 31 21 683 | 12/1982 |
| DE | 10082526 T1 | 7/1999 |
| EP | 0 395 307 A2 | 10/1990 |
| EP | 0 519 415 | 12/1992 |
| EP | 1 430 850 | 12/2003 |
| FR | 2 609 245 | 7/1988 |
| NZ | 266678 | 12/1997 |
| WO | 92/19414 | 11/1992 |
| WO | 93/13816 | 7/1993 |
| WO | 94/26228 | 11/1994 |
| WO | 96/27240 | 9/1996 |
| WO | 96/27327 | 9/1996 |
| WO | 96/32051 | 10/1996 |
| WO | 96/34568 | 11/1996 |
| WO | 96/39914 | 12/1996 |
| WO | 97/18765 | 5/1997 |
| WO | 97/18768 | 5/1997 |
| WO | WO 97/37602 | 10/1997 |
| WO | 68/03117 | 1/1998 |
| WO | 98/03220 | 1/1998 |
| WO | 98 05286 | 2/1998 |
| WO | WO 98/33558 | 8/1998 |
| WO | 99 08614 | 2/1999 |
| WO | WO 00/44297 | 8/2000 |
| WO | WO 00/48644 A3 | 8/2000 |
| WO | WO 00/54685 | 9/2000 |
| WO | WO 00/54686 | 9/2000 |
| WO | WO 01/08545 A2 | 2/2001 |
| WO | WO 02/26147 | 4/2002 |
| WO | WO 02/064209 | 8/2002 |
| WO | WO 02/076318 | 10/2002 |

OTHER PUBLICATIONS

Thermage, Inc., "Motion for Preliminary Injunction", Aug. 6, 2004.

Thermage, Inc., "Memorandum in Support of Motion for Preliminary Injunction", Aug. 6, 2004.

Thermage, Inc, "Declaration of Edward A. Ebbers in Support of Motion for Preliminary Injunction" and attached exhibits A-E, Aug. 6, 2004.

Thermage, Inc. "Declaration of Dr. Maureen Reitman in Support of Motion for Preliminary Injunction" and attached Exhibits A-M, Aug. 6, 2004.

Thermage, Inc. "Declaration of Dave B. Koo in Support of Motion for Preliminary Injunction" and attached Exhibits A-D, Aug. 6, 2004.

Syneron Medical, Ltd., Syneron, Inc., "Declaration of Robert S. McArthur in Support of Syneron's Opposition to Plaintiff's Motion for a Preliminary Injunction"and attached Exhibits 1-25, Aug. 17, 2004.

Syneron Medical, Ltd., Syneron, Inc., "Memorandum in Opposition to Plaintiff's Motion for a Preliminary Injunction", Aug. 27, 2004.

Syneron Medical, Ltd., Syneron, Inc., "Declaration of Dr. Warren S. Grundfest in Support of Syneron's Opposition to Plaintiff's Motion for a Preliminary Injunction" and attached Exhibits A-F, Aug. 27, 2004.

Syneron Medical, Ltd., Syneron, Inc., "Declaration of Dr. Michael Kreindel in Support of Syneron's Opposition to Plaintiff's Motion for a Preliminary Injunction" and attached Exhibit A, Aug. 27, 2004.

Syneron Medical, Ltd., Syneron, Inc., "Declaration of Domenic Serafino in Support of Syneron's Opposition to Plaintiff's Motion for a Preliminary Injunction" and attached Exhibits A-C, Aug. 27, 2004.

Syneron Medical, Ltd., Syneron, Inc., "Declaration of Moshe Mizrahy in Support of Syneron's Opposition to Plaintiff's Motion for a Preliminary Injunction" , Aug. 17, 2004.

Syneron Medical, Ltd., Syneron, Inc., "Syneron Medical Ltd.'s and Syneron, Inc's Answer to Complaint with Jury Demand and Declaratory Judgment, Counterclaim against Thermage, Inc.", Aug. 27, 2004.

Thermage, Inc., "Reply Memorandum re Motion for Preliminary Injunction", Sep. 3, 2004.

Thermage, Inc., "Declaration of John. M. Benassi in Support of Motion for Preliminary Injunction"and attached Exhibits A-B, Sep. 3, 2004.

Thermage, Inc., "Declaration of Paul Davis in Support of Motion for Preliminary Injunction" and attached Exhibits A-C, Sep. 3, 2004.

Thermage, Inc., "Declaration of Robert Gerberich in Support of Motion for Preliminary Injunction", Sep. 3, 2004.

Thermage, Inc., "Declaration of Edward W. Knowlton in Support of Motion for Preliminary Injunction", Sep. 3, 2004.

Thermage, Inc., "Declaration of Richard J. Meader in Support of Motion for Preliminary Injunction", Sep. 3, 2004.

Thermage, Inc., "Declaration of Maureen Reitman in Support of Motion for Preliminary Injunction (Supplemental)", Sep. 3, 2004.

Anvari, et al., "Dynamic Epidermal Cooling in Conjunction with Laser Treatment of Port-Wine Stains: Theoretical and Preliminary Clinical Evaluations", *Laser in Medical Science* 10: 105-112, (Jul. 1995).

Nelson, et al., Abstract: "Dynamic epidermal cooling during pulsed laser treatment of port-wine stain. A new methodology with preliminary clinical evaluation", *Archives of Dermatology*, 131:695-700.

Anvari, et al., "Spatially selective photocoagulation of biological tissues; feasibility study utilizing cryogen spray cooling", *Applied Optics*, vol. 35, No. 19 (Jul. 1996).

Allain, et al. "Isometric Tensions Developed During the Hydrothermal Swelling of Rat Skin", Connective Tissue Research, vol. 7, pp. 697-701, (1990).

Danielson, C. "Age-Related thermal stability and susceptibility to proteolysis of rat bone collagen", . . . chem, Great Britian, pp. 697-701, (1990).

Danielson, C. "Thermal stability of reconstituted collagin fibrils, shrinkage characterisitics upon in vitro maturation", Mechanisms of Ageing and Development, vol. 15, pp. 269-278, (1981).

Kronick, et al. "The locations of collagens with different thermal stabilities in fibrils of bovine recticular dermis". Connective Tissue Research, vol. 18, pp. 123-134, (1988).

Mainster, M.A. "Ophthalmic applications of infrared lasers—thermal considerations", Visual Sci., pp. 414-420, Apr. 1979.

Pearce, et al. "Kinetic models of laser-tissue fusion processes", ISA, paper #93-044, pp. 355-360, (1993).

Adrian, R. M. Treatment of Facial Telangiectasia Using the VersaPulse7 Variable Pulse Width Frequency Doubled Neodymium:YAG Laser: A Case Report.

Chess, C.; Chess, Q. "Cool Laser Optics Treatment of Large Telangiestasia of the Lower Extremities." *J. Dermatol Surg Oncol.* 1993; 19:74-80.

Coulson, W. F. et al. "Nonablative Laser Treatment of Facial Rhytides: Animal Study." Abstract for BiOS '98 Symposium Conference: bo05—Cutaneous Applications of Lasers, Jan. 24-30, 1998, San Jose, CA.

Kincade, K. "Demand for Laser Resurfacing Soars: Quicker Healing, Less Risk of Scarring" *Dermatology Times*. 1995. 16(10).

Fitzpatrick, R. "Treatment of Wrinkles with the UltraPulse $CO_2$ Laser.".

Laser Aesthetics, Inc. "The Cool Touch Laser." Brochure.

Laser Aesthetics, Inc. "Cool Touch Model 130 Technical Specifications." Brochure.

National Health Communications, Inc. "New Laser Eliminates 'Lipstick Bleed'" Press Release Jul. 1993.

* cited by examiner

Electrode with TEC coupled to it:

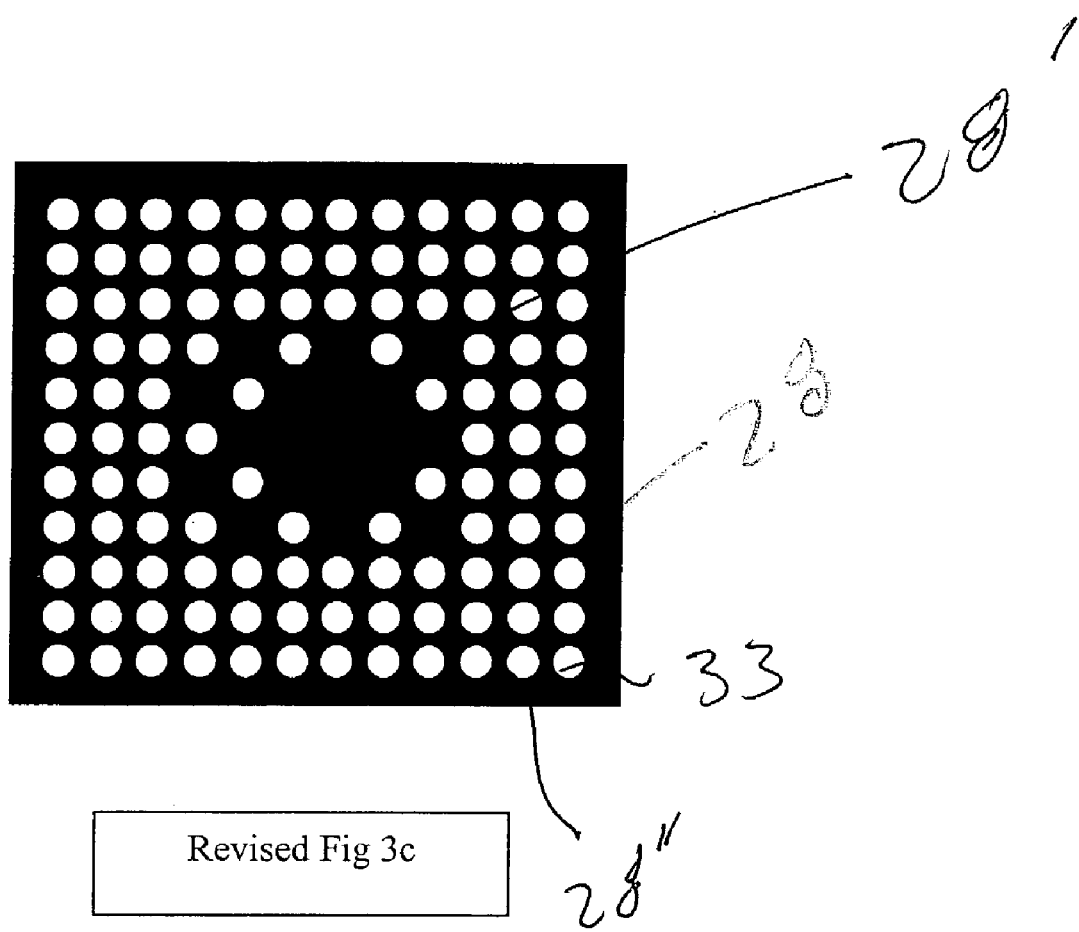
Revised Fig 3c

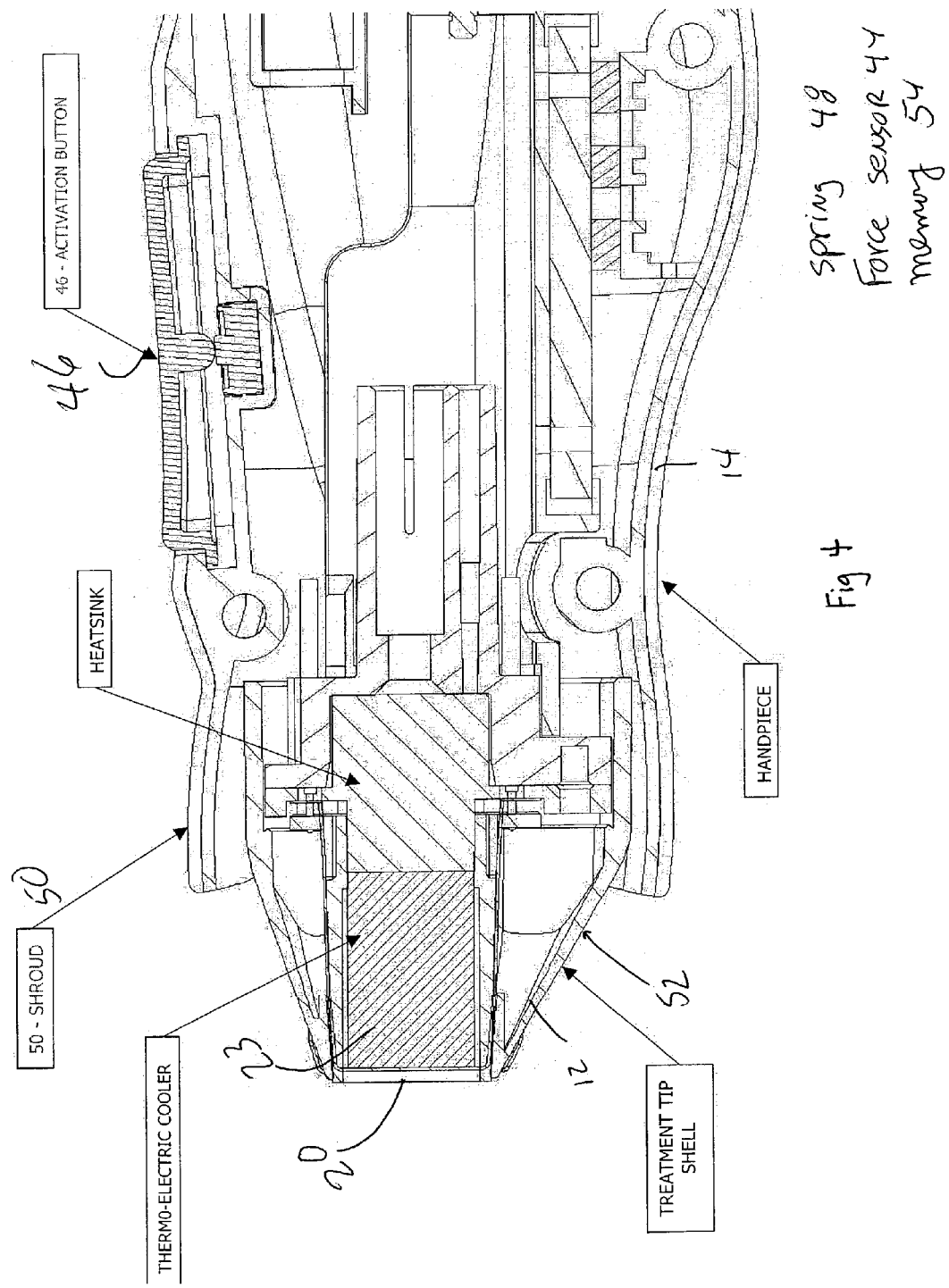

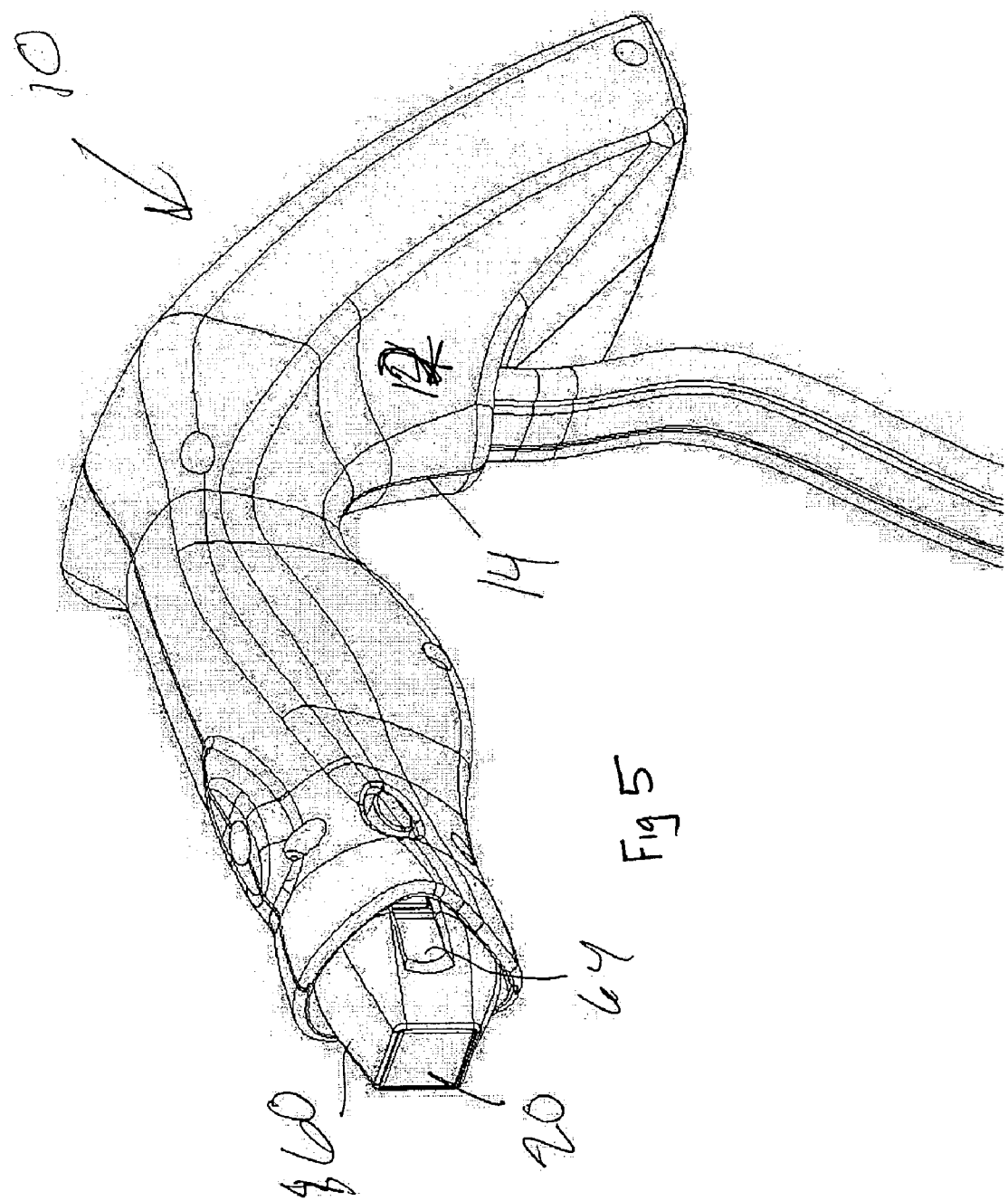

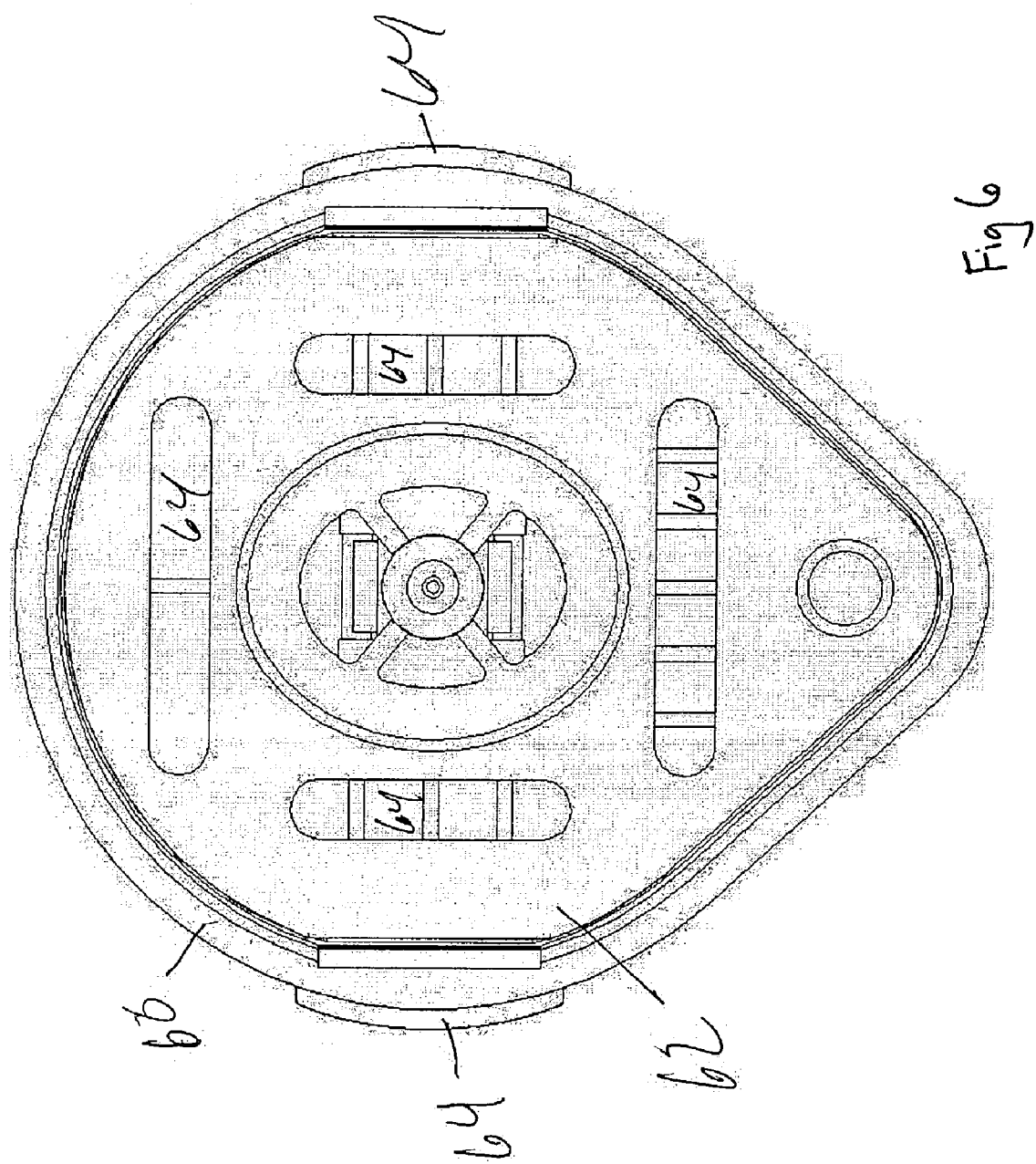

TREATMENT APPARATUS WITH ELECTROMAGNETIC ENERGY DELIVERY DEVICE AND NON-VOLATILE MEMORY

CROSS-REFERENCE TO RELATED APPLICATIONS

This application is a continuation-in-part of U.S. Ser. No. 10/400,187, filed Mar. 25, 2003 which is a continuation-in-part of U.S. Ser. No. 10/072,475 filed Feb. 6, 2002 and a continuation-in-part of U.S. Ser. No. 10/072,610 filed Feb. 6, 2002 both of which are continuations-in-part of U.S. Ser. No. 09/522,275, filed Mar. 9, 2000, which claims the benefit of U.S. Ser. No. 60/123,440, filed Mar. 9, 1999. This application is also a continuation-in-part of U.S. Ser. No. 10/026,870, filed Dec. 20, 2001, now U.S. Pat. No. 6,749,624, which is a continuation of U.S. Ser. No. 09/337,015 filed Jun. 30, 1999, now U.S. Pat. No. 6,350,276, which is a continuation-in-part of U.S. Ser. No. 08/583,815, filed Jan. 5, 1996, now U.S. Pat. No. 6,241,753, U.S. Ser. No. 08/827,237, filed Mar. 28, 1997, now U.S. Pat. No. 6,430,446, U.S. Ser. No. 08/914,681, filed Aug. 19, 1997, now U.S. Pat. No. 5,919,219, and U.S. Ser. No. 08/942,274, filed Sep. 30, 1997, now U.S. Pat. No. 6,425,912 which are all fully incorporated herein by reference.

BACKGROUND OF THE INVENTION

1. Field of the Invention

This invention relates generally to a treatment device, and more particularly to a treatment device that includes an electromagnetic energy delivery device and a non-volatile memory.

2. Description of Related Art

The human skin is composed of two elements: the epidermis and the underlying dermis. The epidermis with the stratum corneum serves as a biological barrier to the environment. In the basilar layer of the epidermis, pigment-forming cells called melanocytes are present. They are the main determinants of skin color.

The underlying dermis provides the main structural support of the skin. It is composed mainly of an extra-cellular protein called collagen. Collagen is produced by fibroblasts and synthesized as a triple helix with three polypeptide chains that are connected with heat labile and heat stable chemical bonds. When collagen-containing tissue is heated, alterations in the physical properties of this protein matrix occur at a characteristic temperature. The structural transition of collagen contraction occurs at a specific "shrinkage" temperature. The shrinkage and remodeling of the collagen matrix with heat is the basis for the technology. Although the technology can be deployed to effect other changes to the skin, skin appendages (sweat glands, sebaceous glands, hair follicles, etc.), or subcutaneous tissue structures.

Collagen crosslinks are either intramolecular (covalent or hydrogen bond) or intermolecular (covalent or ionic bonds). The thermal cleavage of intramolecular hydrogen crosslinks is a scalar process that is created by the balance between cleavage events and relaxation events (reforming of hydrogen bonds). No external force is required for this process to occur. As a result, intermolecular stress is created by the thermal cleavage of intramolecular hydrogen bonds. Essentially, the contraction of the tertiary structure of the molecule creates the initial intermolecular vector of contraction.

Collagen fibrils in a matrix exhibit a variety of spatial orientations. The matrix is lengthened if the sum of all vectors acts to lengthen the fibril. Contraction of the matrix is facilitated if the sum of all extrinsic vectors acts to shorten the fibril. Thermal disruption of intramolecular hydrogen bonds and mechanical cleavage of intermolecular crosslinks is also affected by relaxation events that restore preexisting configurations. However, a permanent change of molecular length will occur if crosslinks are reformed after lengthening or contraction of the collagen fibril. The continuous application of an external mechanical force will increase the probability of crosslinks forming after lengthening or contraction of the fibril.

Hydrogen bond cleavage is a quantum mechanical event that requires a threshold of energy. The amount of (intramolecular) hydrogen bond cleavage required corresponds to the combined ionic and covalent intermolecular bond strengths within the collagen fibril. Until this threshold is reached, little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and nonpolar regions in the lengthened or contracted fibril.

Cleavage of collagen bonds also occurs at lower temperatures but at a lower rate. Low-level thermal cleavage is frequently associated with relaxation phenomena in which bonds are reformed without a net change in molecular length. An external force that mechanically cleaves the fibril will reduce the probability of relaxation phenomena and provides a means to lengthen or contract the collagen matrix at lower temperatures while reducing the potential of surface ablation.

Soft tissue remodeling is a biophysical phenomenon that occurs at cellular and molecular levels. Molecular contraction or partial denaturization of collagen involves the application of an energy source, which destabilizes the longitudinal axis of the molecule by cleaving the heat labile bonds of the triple helix. As a result, stress is created to break the intermolecular bonds of the matrix. This is essentially an immediate extra-cellular process, whereas cellular contraction requires a lag period for the migration and multiplication of fibroblasts into the wound as provided by the wound healing sequence. In higher developed animal species, the wound healing response to injury involves an initial inflammatory process that subsequently leads to the deposition of scar tissue.

The initial inflammatory response consists of the infiltration by white blood cells or leukocytes that dispose of cellular debris. Seventy-two hours later, proliferation of fibroblasts at the injured site occurs. These cells differentiate into contractile myofibroblasts, which are the source of cellular soft tissue contraction. Following cellular contraction, collagen is laid down as a static supporting matrix in the tightened soft tissue structure. The deposition and subsequent remodeling of this nascent scar matrix provides the means to alter the consistency and geometry of soft tissue for aesthetic purposes.

In light of the preceding discussion, there are a number of dermatological procedures that lend themselves to treatments which deliver thermal energy to the skin and underlying tissue to cause a contraction of collagen, and/or initiate a would healing response. Such procedures include skin remodeling/resurfacing, wrinkle removal, and treatment of the sebaceous glands, hair follicles adipose tissue and spider veins.

Currently available technologies that deliver thermal energy to the skin and underlying tissue include Radio Frequency (RF), optical (laser) and other forms of electromagnetic energy as well as ultrasound and direct heating with a hot surface. However, these technologies have a number of technical limitations and clinical issues which limit the effectiveness of the treatment and/or preclude treatment altogether.

These issues include the following: i) achieving a uniform thermal effect across a large area of tissue, ii) controlling the depth of the thermal effect to target selected tissue and prevent unwanted thermal damage to both target and non-target tissue, iii) reducing adverse tissue effects such as burns, redness blistering, iv) replacing the practice of delivery energy/treatment in a patchwork fashion with a more continuous delivery of treatment (e.g. by a sliding or painting motion), v) improving access to difficult-to-reach areas of the skin surface and vi) reducing procedure time and number of patient visits required to complete treatment. As will be discussed herein the current invention provides an apparatus for solving these and other limitations.

One of the key shortcomings of currently available RF technology for treating the skin is the edge effect phenomenon. In general, when RF energy is being applied or delivered to tissue through an electrode which is in contact with that tissue, the current concentrate around the edges of the electrode, sharp edges in particular. This effect is generally known as the edge effect. In the case of a circular disc electrode, the effect manifests as a higher current density around the perimeter of that circular disc and a relatively low current density in the center. For a square-shaped electrode there is typically a high current density around the entire perimeter, and an even higher current density at the corners.

Edge effects cause problems in treating the skin for several reasons. First, they result in a non-uniform thermal effect over the electrode surface. In various treatments of the skin, it is important to have a uniform thermal effect over a relatively large surface area, particularly for dermatological treatments. Large in this case being on the order of several square millimeters or even several square centimeters. In electrosurgical applications for cutting tissue, there typically is a point type applicator designed with the goal of getting a hot spot at that point for cutting or even coagulating tissue. However, this point design is undesirable for creating a reasonably gentle thermal effect over a large surface area. What is needed is an electrode design to deliver uniform thermal energy to skin and underlying tissue without hot spots.

A uniform thermal effect is particularly important when cooling is combined with heating in skin/tissue treatment procedure. As is discussed below, a non-uniform thermal pattern makes cooling of the skin difficult and hence the resulting treatment process as well. When heating the skin with RF energy, the tissue at the electrode surface tends to be warmest with a decrease in temperature moving deeper into the tissue. One approach to overcome this thermal gradient and create a thermal effect at a set distance away from the electrode is to cool the layers of skin that are in contact with the electrode. However, cooling of the skin is made difficult if there is a non-uniform heating pattern.

If the skin is sufficiently cooled such that there are no burns at the corners of a square or rectangular electrode, or at the perimeter of a circular disc electrode, then there will probably be overcooling in the center and there won't be any significant thermal effect (i.e. tissue heating) under the center of the electrode. Contrarily, if the cooling effect is decreased to the point where there is a good thermal effect in the center of the electrode, then there probably will not be sufficient cooling to protect tissue in contact with the edges of the electrode. As a result of these limitations, in the typical application of a standard electrode there is usually an area of non-uniform treatment and/or burns on the skin surface. So uniformity of the heating pattern is very important. It is particularly important in applications treating skin where collagen-containing layers are heated to produce a collagen contraction response for tightening of the skin. For this and related applications, if the collagen contraction and resulting skin tightening effect are non-uniform, then a medically undesirable result may occur.

There is a need for an improved electromagnetic energy delivery device. There is a further need for an electromagnetic energy delivery device that is suitable for cosmetic applications.

SUMMARY OF THE INVENTION

Accordingly, an object of the present invention is to provide an improved apparatus for cooling a skin surface that includes an electromagnetic energy delivery device.

Another object of the present invention is to provide an apparatus for cooling a skin surface that includes an electromagnetic energy delivery device and resources that permit different levels of cooling during a treatment.

Yet another object of the present invention is to provide an apparatus for cooling a skin surface that includes an electromagnetic energy delivery device and cooling member that can deliver different levels of cooling at different times of treatment.

A further object of the present invention is to provide an apparatus for cooling a skin surface that includes an electromagnetic energy delivery device and a memory that stores information to facilitate operation of at least one of a cooling member, or an associated electromagnetic energy source.

These and other objects of the present invention are achieved in an apparatus for cooling a skin surface that includes a support structure coupled to an electromagnetic energy delivery device. The electromagnetic energy delivery device is configured to be coupled to an electromagnetic energy source. A cooling member is coupled to the electromagnetic energy delivery device and is configured to create a reverse thermal gradient through a skin surface. A memory is coupled to the electromagnetic energy delivery device and is positioned at the support structure or the electromagnetic energy delivery device. The memory is configured to store information to facilitate operation of at least one of the cooling member, and the electromagnetic energy source. Resources are coupled to the cooling member to permit different levels of cooling at different times of treatment.

In another embodiment of the present invention, an apparatus for cooling a skin surface includes an electromagnetic energy delivery device configured to be coupled to an electromagnetic energy source. A cooling member is coupled to the electromagnetic energy delivery device and is configured to create a reverse thermal gradient through a skin surface. The cooling member provides different levels of cooling at different times of treatment. A memory is coupled to the electromagnetic energy delivery device and is positioned at the support structure or the electromagnetic energy delivery device. The memory is configured to store information to facilitate operation of at least one of the cooling member, and the electromagnetic energy source.

In another embodiment of the present invention, an apparatus for cooling a skin surface includes a support structure and an electromagnetic energy delivery device coupled to the support structure. the electromagnetic energy delivery device is configured to be coupled to an electromagnetic energy source. A cooling member is coupled to the electromagnetic energy delivery device and is configured to create a reverse thermal gradient through a skin surface. A memory is coupled to the electromagnetic energy delivery device and is positioned at the support structure or the electromagnetic energy delivery device. The memory is configured to store information to facilitate operation of at least one of the cooling member, and the electromagnetic energy source. A sensor is coupled to the electromagnetic energy delivery device.

In another embodiment of the present invention, an apparatus for treating a tissue includes a device assembly coupled to an electromagnetic energy delivery device that is configured to be coupled to an electromagnetic energy source. A cooling member is configured to create a reversal thermal gradient through a skin surface to an underlying tissue. A sensor is coupled to the dielectric electrode. A memory is coupled to the electromagnetic energy delivery device. The memory is configured to store information to facilitate operation of at least one of the electromagnetic energy delivery device, the cooling member, and an electromagnetic energy source.

In another embodiment of the present invention, an apparatus for treating a tissue site includes a device coupled to a first electromagnetic energy delivery device and a second electromagnetic energy delivery device. The first and second electromagnetic energy delivery devices are configured to be coupled to first and second electromagnetic energy delivery sources respectively. A cooling member is configured to create a reversal thermal gradient through the skin to an underlying tissue. A memory is coupled to at least one of the first and second electromagnetic energy delivery devices. The memory is configured to store information to facilitate operation of at least one of the first electromagnetic energy delivery device, the second electromagnetic energy delivery device, the cooling member, the first electromagnetic energy source and the second electromagnetic energy source.

In another embodiment of the present invention, a treatment apparatus includes a treatment device assembly coupled to an electromagnetic energy delivery device assembly. The electromagnetic energy delivery device assembly includes a tissue interface surface and is configured to be coupled to an electromagnetic energy source. A cooling member is coupled to the treatment device assembly and is configured to provide cooling to at least a portion of the tissue interface surface. The electromagnetic energy delivery device assembly is configured to provide conductive cooling to a tissue positioned adjacent to the tissue interface surface. A memory is coupled to the electromagnetic energy delivery device. The memory is configured to store information to facilitate operation of at least one of the electromagnetic energy delivery device, the cooling member and the electromagnetic energy source.

DETAILED DESCRIPTION OF THE PREFERRED EMBODIMENTS

In various embodiments, the present invention provides methods for treating a tissue site. In one embodiment, an energy delivery surface of an energy delivery device is coupled to a skin surface. The coupling can be a direct, in contact, placement of the energy delivery surface of the energy delivery device on the skin surface, or distanced relationship between the two with or without a media to conduct energy to the skin surface from the energy delivery surface of the energy delivery device. The skin surface is cooled sufficiently to create a reverse thermal gradient where a temperature of the skin surface is less than an underlying tissue. Energy is delivered from the energy delivery device to the underlying tissue area, resulting in a tissue effect at the skin surface.

Figure 1A:
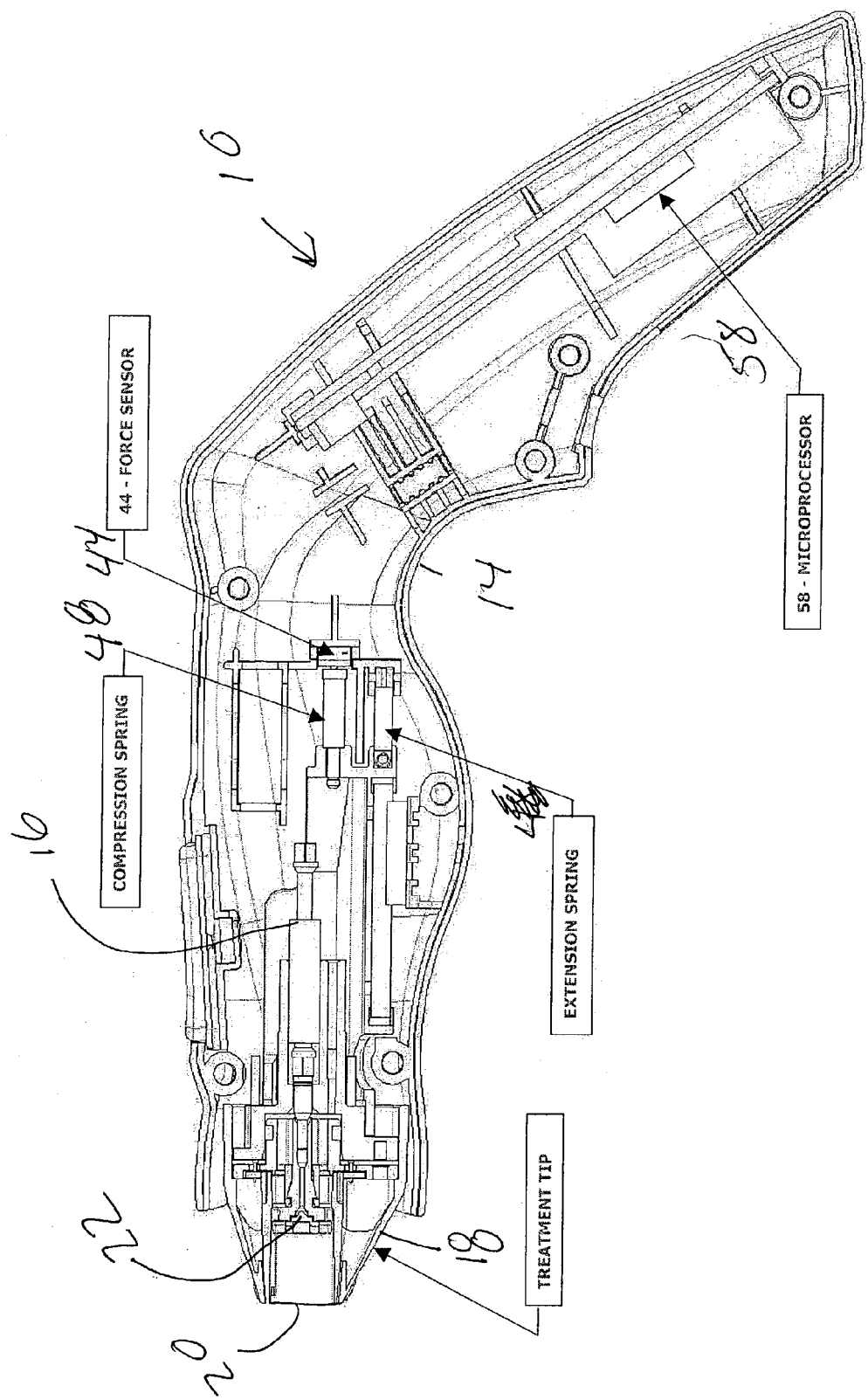
FIG. 1(a) is a cross-sectional view of one embodiment of the handpiece of the present invention.

Referring now to FIG. 1(a), the methods of present invention can be achieved with the use of a handpiece 10. Handpiece 10 is coupled with a handpiece assembly 12 that includes a handpiece housing 14 and a cooling fluidic medium valve member 16. Handpiece housing 14 is configured to be coupled to a suitable electromagnetic energy delivery device, including but not limited to an electrode assembly 18. Electrode assembly 18 has a least one RF electrode 20 that is capacitively coupled to a skin surface when at least a portion of RF electrode 20 is in contact with the skin surface. Without limiting the scope of the present invention, RF electrode 20 can have a thickness in the range of 0.010 to 1.0 mm.

Handpiece 10 provides a more uniform thermal effect in tissue at a selected depth, while preventing or minimizing thermal damage to the skin surface and other non-target tissue. Handpiece 10 is coupled to an electromagnetic energy source, including but not limited to an RF generator, creating at least a portion of the System. RF electrode 20 can be operated either in mono-polar or bi-polar modes. Handpiece 10 is configured to reduce, or preferably eliminate edge effects and hot spots. The result is an improved aesthetic result/clinical outcome with an elimination/reduction in adverse effects and healing time.

A fluid delivery member 22 is coupled to cooling fluidic medium valve member 16. Fluid delivery member 22 and cooling fluidic medium valve member 16 collectively form a cooling fluidic medium dispensing assembly. Fluid delivery member 22 is configured to provide an atomizing delivery of a cooling fluidic medium to RF electrode 20. The atomizing delivery is a mist or fine spray. A phase transition, from liquid to gas, of the cooling fluidic medium occurs when it hits the surface of RF electrode 20. The transition from liquid to gas creates the cooling. If the transition before the cooling fluidic medium hits RF electrode 20 the cooling of RF electrode 20 will not be as effective.

Figure 1B:
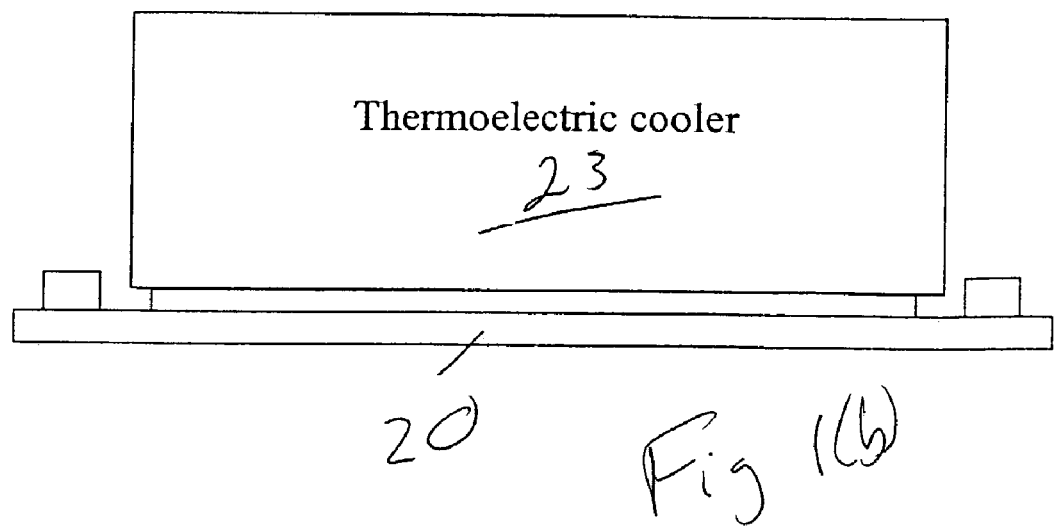
FIG. 1(b) is a cross-sectional view of another embodiment of the RF device with a thermoelectric cooler.

In another embodiment, illustrated in FIG. 1(b), a thermoelectric cooler 23 is utilized in place of cooling fluidic medium valve member 16 and fluid delivery member 22.

In one embodiment, the cooling fluidic medium is a cryogenic spray, commercially available from Honeywell, Morristown, N.J. A specific example of a suitable cryogenic spray is R134A$_2$, available from Refron, Inc., 38-18 33$^{rd}$ St., Long Island City, N.Y. 11101. The use of a cryogenic cooling fluidic medium provides the capability to use a number of different types of algorithms for skin treatment. For example, the cryogenic cooling fluidic medium can be applied milliseconds before and after the delivery of RF energy to the desired tissue. This is achieved with the use of cooling fluidic medium valve member 16 coupled to a cryogen supply, including but not limited to a compressed gas canister. In various embodiments, cooling fluidic medium valve member 16 can be coupled to a computer control system and/or manually controlled by the physician by means of a foot switch or similar device.

Providing a spray, or atomization, of cryogenic cooling fluidic medium is particularly suitable because of it provides an availability to implement rapid on and off control. Cryogenic cooling fluidic medium allows more precise temporal control of the cooling process. This is because cooling only occurs when the refrigerant is sprayed and is in an evaporative state, the latter being a very fast short-lived event. Thus, cooling ceases rapidly after the cryogenic cooling fluidic medium is stopped. The overall effect is to confer very precise time on-off control of cryogenic cooling fluidic medium.

Figure 2:
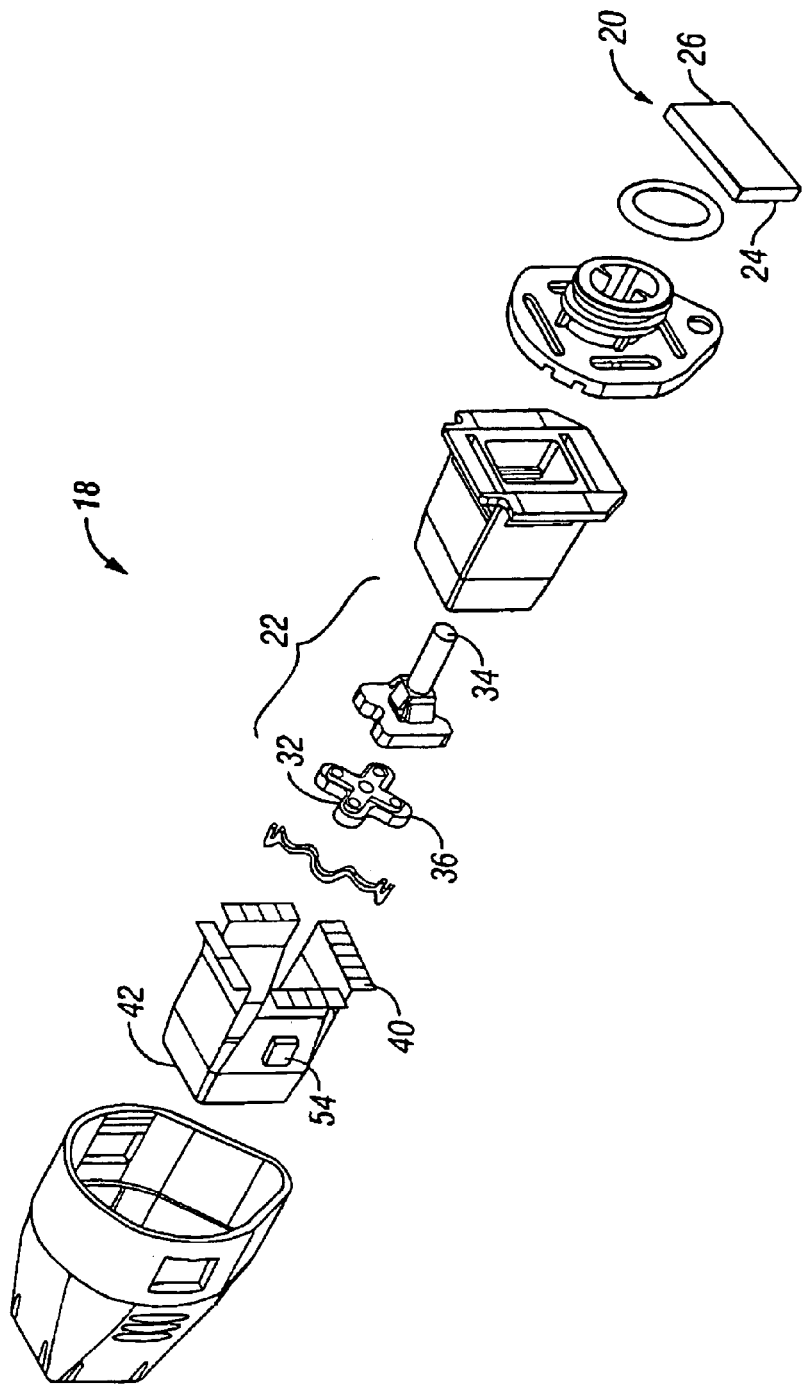
FIG. 2 is an exploded view of the FIG. 1 RF electrode assembly.

Referring now to FIG. 2, fluid delivery member 22 and thermo-electric cooler 23 can be positioned in handpiece housing 14 or electrode assembly 18. Fluid delivery member 22 is configured to controllably deliver a cooling fluidic medium. Fluid delivery member 22 and thermo-electric cooler 23 cool a back surface 24 of RF electrode 20 and maintain back surface 24 at a desired temperature. The cooling fluidic medium evaporatively cools RF electrode 20 and maintains a substantially uniform temperature of front surface 26 of RF electrode 20. Fluid delivery member 22 evaporatively cools back surface 24. Front surface 26 may or may not be flexible and conformable to the skin, but it will still have sufficient strength and/or structure to provide good thermal coupling when pressed against the skin surface.

RF electrode 20 then conductively cools a skin surface that is adjacent to a front surface 26 of RF electrode 20. Suitable fluidic media include a variety of refrigerants such as R134A and freon.

Fluid delivery member 22 is configured to controllably deliver the cooling fluidic medium to back surface 24 in substantially any orientation of front surface 26 relative to a direction of gravity. A geometry and positioning of fluid delivery member 22 is selected to provide a substantially uniform distribution of cooling fluidic medium on back surface 24. The delivery of the cooling fluidic medium can be by spray of droplets or fine mist, flooding back surface 24, and the like. Cooling occurs at the interface of the cooling fluidic medium with atmosphere, which is where evaporation occurs. If there is a thick layer of fluid on back surface 24 the heat removed from the treated skin will need to pass through the thick layer of cooling fluidic medium, increasing thermal resistance. To maximize cooling rates, it is desirable to apply a very thin layer of cooling fluidic medium. If RF electrode 20 is not horizontal, and if there is a thick layer of cooling fluidic medium, or if there are large drops of cooling fluidic medium on back surface 24, the cooling fluidic medium can run down the surface of RF electrode 20 and pool at one edge or corner, causing uneven cooling. Therefore, it is desirable to apply a thin layer of cooling fluidic medium with a fine spray. Thermo-electric cooler 23 achieves these same results but without delivering a cooling medium. Thermo-electric cooler 23 is cold on the side that is adjacent to or in contact with surface 24, while its opposing side becomes warmer.

Figure 3A:
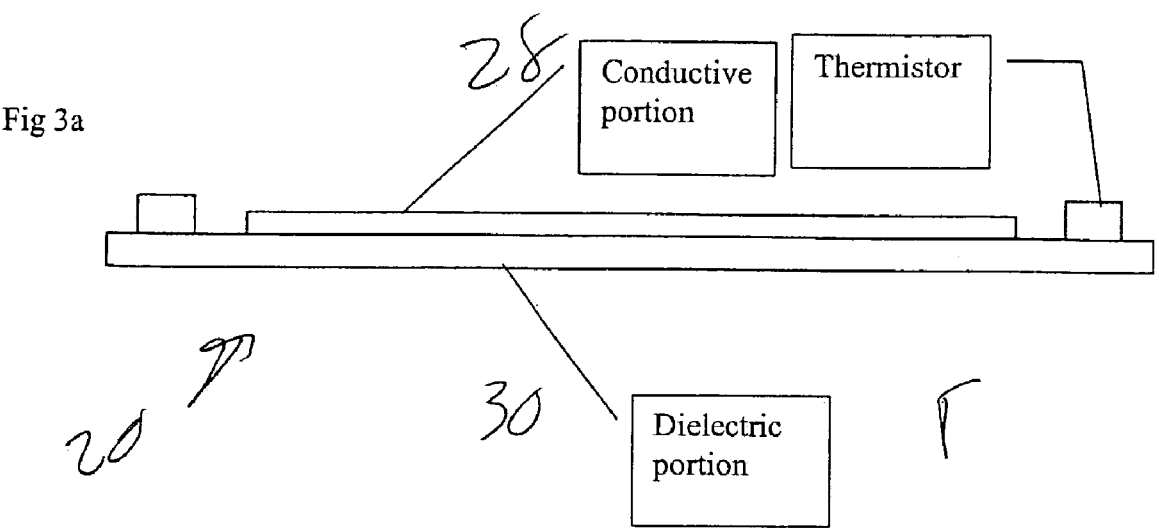
FIG. 3(a) is a close-up view of one embodiment of an RF electrode of the present invention.

In various embodiments, RF electrode 20, as illustrated in FIG. 3(a), has a conductive portion 28 and a dielectric portion 30. Conductive portion 28 can be a metal including but not limited to copper, gold, silver, aluminum and the like. Dielectric portion 30 can be made of a variety of different materials including but not limited to polyimide, Teflon® and the like, silicon nitride, polysilanes, polysilazanes, polyimides, Kapton and other polymers, antenna dielectrics and other dielectric materials well known in the art. Other dielectric materials include but are not limited to polymers such as polyester, silicon, sapphire, diamond, zirconium-toughened alumina (ZTA), alumina and the like. Dielectric portion 30 can be positioned around at least a portion, or the entirety of a periphery of conductive portion 28. In another embodiment, RF electrode 20 is made of a composite material, including but not limited to gold-plated copper, copper-polyimide, silicon/silicon-nitride and the like.

Dielectric portion 30 creates an increased impedance to the flow of electrical current through RF electrode 20. This increased impedance causes current to travel a path straight down through conductive portion 28 to the skin surface. Electric field edge effects, caused by a concentration of current flowing out of the edges of RF electrode 20, are reduced.

Figure 3B:
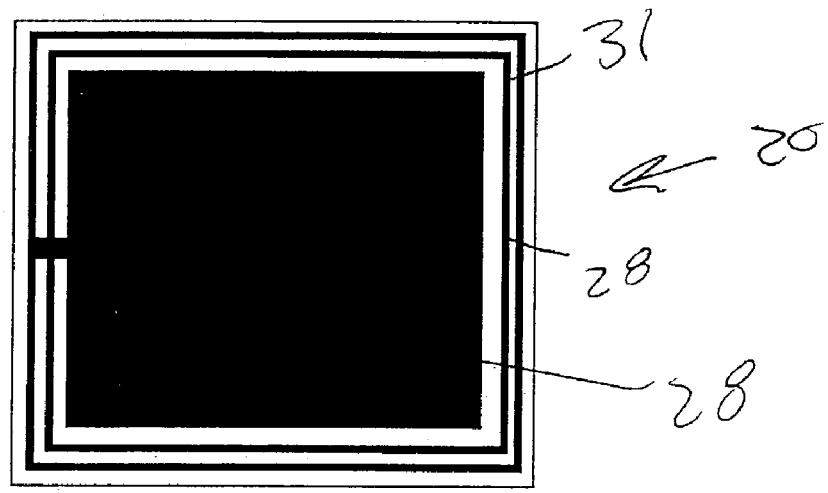
FIG. 3(b) illustrates one embodiment of an RF electrode, that can be utilized with the present invention, with an outer edge geometry configured to reduce an amount of capacitively coupled area the outer edge.
Figure 3A:
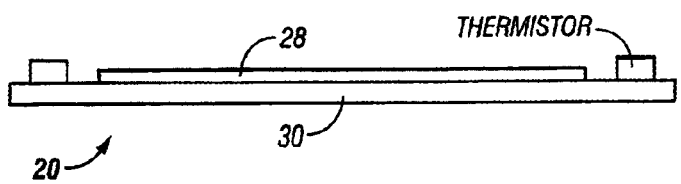
Figure 3B:
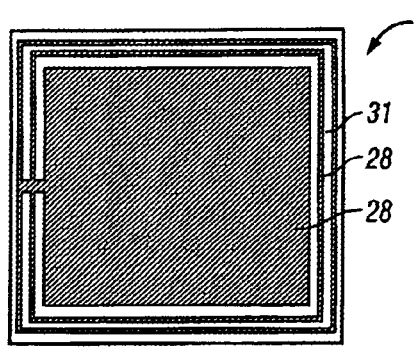
Figure 3C:
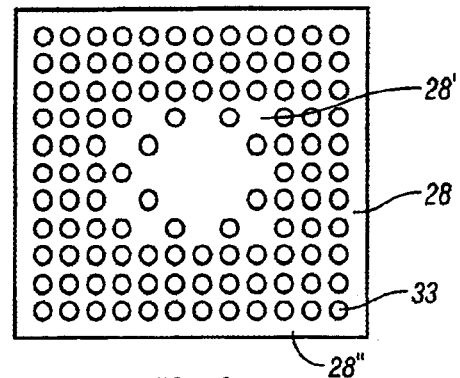
FIG. 3(c) illustrates an one embodiment of an RF electrode, that can be utilized with the present invention, that has voids where there is little if any conductive material.

Dielectric portion 30 produces a more uniform impedance through RF electrode 20 and causes a more uniform current to flow through conductive portion 28. The resulting effect minimizes or even eliminates, edge effects around the edges of RF electrode 20. As shown in FIG. 3(c), RF electrode 20 can have voids 33 where there is little or no conductive material. Creating voids 33 in the conductive material alters the electric field. The specific configuration of voids can be used to minimize edge effect, or alter the depth, uniformity or shape of the electric field. Under a portion 28' of the RF electrode 20 with solid conductive material the electric field is deeper. Under a portion 28" of RF electrode 20 with more voids, the electric field is shallower. By combining different densities of conductive material, an RF electrode 20 is provided to match the desired heating profile.

In one embodiment, conductive portion 28 adheres to dielectric portion 30 which can be a substrate with a thickness, by way of example and without limitation, of about 0.001". This embodiment is similar to a standard flex circuit board material commercially available in the electronics industry. In this embodiment, dielectric portion 30 is in contact with the tissue, the skin, and conductive portion 28 is separated from the skin.

The thickness of the dielectric portion 30 can be decreased by growing conductive portion 28 on dielectric portion 30 using a variety of techniques, including but not limited to, sputtering, electro deposition, chemical vapor deposition, plasma deposition and other deposition techniques known in the art. Additionally, these same processes can be used to deposit dielectric portion 30 onto conductive portion 28. In one embodiment dielectric portion 30 is an oxide layer which can be grown on conductive portion 28. An oxide layer has a low thermal resistance and improves the cooling efficiency of the skin compared with many other dielectrics such as polymers.

In various embodiments, RF electrode 20 is configured to inhibit the capacitive coupling to tissue along its outside edge 31. Referring to FIG. 3(b) RF electrode 20 can have an outer edge 31 with a geometry that is configured to reduce an amount of capacitively coupled area at outer edge 31. Outer edge 31 can have less of the conductive portion 28 material. This can be achieved by different geometries, including but not limited to a scalloped geometry, and the like. The total length of outer edge 31 can be increased, with different geometries, and the total area that is capacitively coupled to tissue is reduced. This produces a reduction in energy generation around outer edge 31.

Alternatively, the dielectric material can be applied in a thicker layer at the edges, reducing the electric field at the edges. A further alternative is to configure the cooling to cool more aggressively at the edges to compensate for any electric field edge effect.

Fluid delivery member 22 has an inlet 32 and an outlet 34. Outlet 34 can have a smaller cross-sectional area than a cross-sectional area of inlet 32. In one embodiment, fluid delivery member 22 is a nozzle 36.

Cooling fluidic medium valve member 16 can be configured to provide a pulsed delivery of the cooling fluidic medium. Pulsing the delivery of cooling fluidic medium is a simple way to control the rate of cooling fluidic medium application. In one embodiment, cooling fluidic medium valve member 16 is a solenoid valve. An example of a suitable solenoid valve is a solenoid pinch valve manufactured by the N-Research Corporation, West Caldwell, N.J. If the fluid is pressurized, then opening of the valve results in fluid flow. If the fluid is maintained at a constant pressure, then the flow rate is constant and a simple open/close solenoid valve can be used, the effective flow rate being determined by the pulse duty cycle. A higher duty cycle, close to 100% increases cooling, while a lower duty cycle, closer to 0%, reduces cooling. The duty cycle can be achieved by turning on the valve for a short duration of time at a set frequency. The duration of the open time can be 1 to 50 milliseconds or longer. The frequency of pulsing can be 1 to 50 Hz or faster.

Alternatively, cooling fluidic medium flow rate can be controlled by a metering valve or controllable-rate pump such as a peristaltic pump. One advantage of pulsing is that it is easy to control using simple electronics and control algorithms.

Electrode assembly 18 is sufficiently sealed so that the cooling fluidic medium does not leak from back surface 24 onto a skin surface in contact with a front surface of RF electrode 20. This helps provide an even energy delivery through the skin surface. In one embodiment, electrode assembly 18, and more specifically RF electrode 20, has a geometry that creates a reservoir at back surface 24 to hold and gather cooling fluidic medium that has collected at back surface 24. Back surface 24 can be formed with "hospital corners" to create this reservoir. Optionally, electrode assembly 18 includes a vent that permits vaporized cooling fluidic medium to escape from electrode assembly 18.

The vent prevents pressure from building up in electrode assembly 18. The vent can be a pressure relief valve that is vented to the atmosphere or a vent line. When the cooling fluidic medium comes into contact with RF electrode 20 and evaporates, the resulting gas pressurizes the inside of electrode assembly 18. This can cause RF electrode 20 to partially inflate and bow out from front surface 26. The inflated RF electrode 20 can enhance the thermal contact with the skin and also result in some degree of conformance of RF electrode 20 to the skin surface. An electronic controller can be provided. The electronic controller sends a signal to open the vent when a programmed pressure has been reached.

Various leads 40 are coupled to RF electrode 20. One or more thermal sensors 42 are coupled to RF electrode. If will be appreciated that other sensors, including but not limited to voltage, current, power and the like, can also be included. Suitable thermal sensors 42 include but are not limited to thermocouples, thermistors, infrared photo-emitters and a thermally sensitive diode. In one embodiment, a thermal sensor 42 is positioned at each corner of RF electrode 20. A sufficient number of thermal sensors 42 are provided in order to acquire sufficient thermal data of the skin surface or the back surface 24 of the electrode 20. Thermal sensors 42 are electrically isolated from RF electrode 20. In another embodiment, at least one sensor 42 is positioned at back surface 24 of RF electrode and detects the temperature of back surface 24 in response to the delivery of cooling fluidic medium.

Thermal sensors 42 measure temperature and can provide feedback for monitoring temperature of RF electrode 20 and/or the tissue during treatment. Thermal sensors 42 can be thermistors, thermocouples, thermally sensitive diodes, capacitors, inductors or other devices for measuring temperature. Preferably, thermal sensors 42 provide electronic feedback to a microprocessor of the RF generator coupled to RF electrode 20 in order to facilitate control of the treatment.

Measurements from thermal sensors 42 can be used to help control the rate of application of cooling fluidic medium. For example, a cooling control algorithm can be used to apply cooling fluidic medium to RF electrode 20 at a high flow rate until the temperature fell below a target temperature, and then slow down or stop. A PID, or proportional-integral-differential, algorithm can be used to precisely control RF electrode 20 temperature to a predetermined value.

Thermal sensors 42 can be positioned on back surface 24 of RF electrode 20 away from the tissue. This configuration is preferable for controlling the temperature of the RF electrode 20. Alternatively, thermal sensors 42 can be positioned on front surface 26 of RF electrode 10 in direct contact with the tissue. This embodiment can be more suitable for monitoring tissue temperature. Algorithms are utilized with thermal sensors 42 to calculate a temperature profile of the treated tissue. Thermal sensors 42 can be used to develop a temperature profile of the skin which is then used for process control purposes to assure that the proper amounts of heating and cooling are delivered to achieve a desired elevated deep tissue temperature while maintaining skin tissue layers below a threshold temperature and avoid thermal injury.

The physician can use the measured temperature profile to assure that he stays within the boundary of an ideal/average profile for a given type of treatment. Thermal sensors 42 can be used for additional purposes. When the temperature of thermal sensors 42 is monitored it is possible to detect when RF electrode 20 is in contact with the skin surface. This can be achieved by detecting a direct change in temperature when skin contact is made or examining the rate of change of temperature which is affected by contact with the skin. Similarly, if there is more than one thermal sensor 42, the thermal sensors 42 can be used to detect whether a portion of RF electrode 20 is lifted or out of contact with skin. This can be important because the current density (amperes per unit area) delivered to the skin can vary if the contact area changes. In particular, if part of the surface of RF electrode 20 is not in contact with the skin, the resulting current density is higher than expected.

Referring again to FIG. 1(a), a force sensor 44 is also coupled to electrode assembly 18. Force sensor 44 detects an amount of force applied by electrode assembly 18, via the physician, against an applied skin surface. Force sensor 44 zeros out gravity effects of the weight of electrode assembly 18 in any orientation of front surface 26 of RF electrode 20 relative to a direction of gravity. Additionally, force sensor 44 provides an indication when RF electrode 20 is in contact with a skin surface. Force sensor 44 also provides a signal indicating that a force applied by RF electrode 20 to a contacted skin surface is, (i) above a minimum threshold or (ii) below a maximum threshold.

Figure 4:
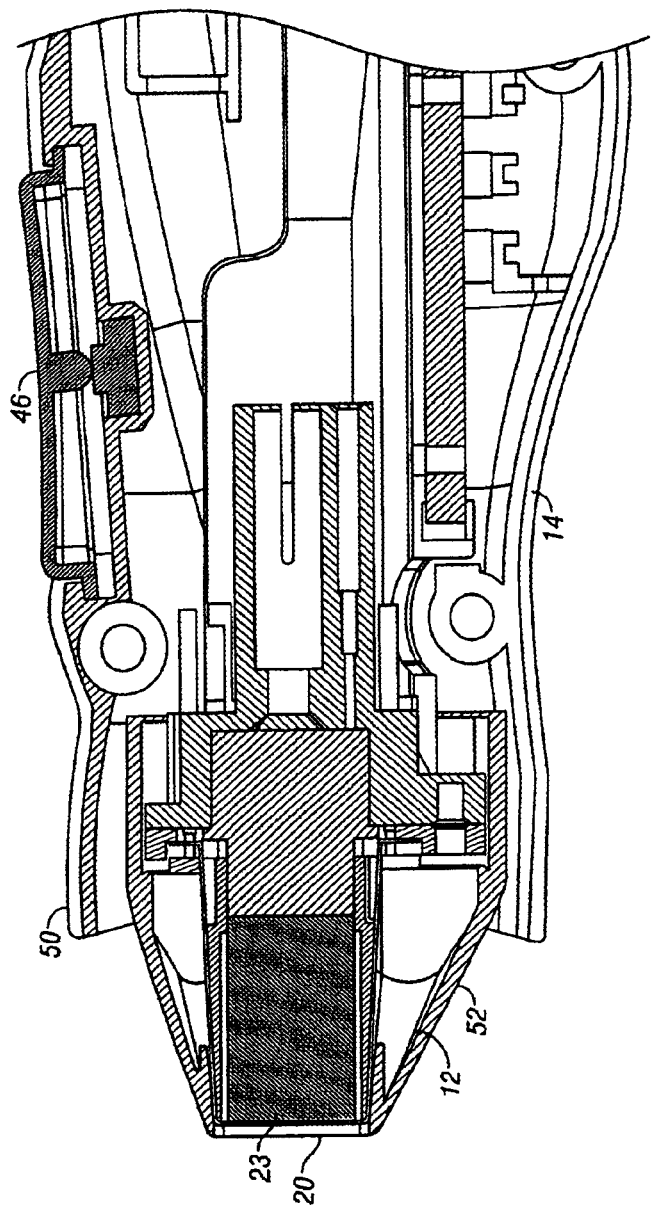
FIG. 4 is a cross-sectional view of the RF electrode assembly from FIG. 1.

As illustrated in FIG. 4, an activation button 46 is used in conjunction with the force sensor. Just prior to activating RF electrode 20, the physician holds handpiece 10 in position just off the surface of the skin. The orientation of handpiece 10 can be any angle relative to the direction of gravity. To arm handpiece 10, the physician can press activation button 46 which tares force sensor 44, by setting it to read zero. This cancels the force due to gravity in that particular treatment orientation. This method allows consistent force application of RF electrode 20 to the skin surface regardless of the angle of handpiece 10 relative to the direction of gravity.

RF electrode 20 can be a flex circuit, which can include trace components. Additionally, thermal sensor 42 and force sensor 44 can be part of the flex circuit. Further, the flex circuit can include a dielectric that forms a part of RF electrode 20.

Electrode assembly 18 can be moveably positioned within handpiece housing 12. In one embodiment, electrode assembly 18 is slideably moveable along a longitudinal axis of handpiece housing 12.

Electrode assembly 18 can be rotatably mounted in handpiece housing 12. Additionally, RF electrode 20 can be rotatably positioned in electrode assembly 18. Electrode assembly 18 can be removably coupled to handpiece housing 12 as a disposable or non-disposable RF device 52.

For purposes of this disclosure, electrode assembly 18 is the same as RF device 52. Once movably mounted to handpiece housing 12, RF device 52 can be coupled to handpiece housing 12 via force sensor 44. Force sensor 44 can be of the type that is capable of measuring both compressive and tensile forces. In other embodiments, force sensor 44 only measures compressive forces, or only measures tensile forces.

RF device 52 can be spring-loaded with a spring 48. In one embodiment, spring 48 biases RF electrode 20 in a direction toward handpiece housing 12. This pre-loads force sensor 44 and keeps RF device 52 pressed against force sensor 44. The pre-load force is tared when activation button 46 is pressed just prior to application of RF electrode 20 to the skin surface.

A shroud 50 is optionally coupled to handpiece 10. Shroud 50 serves to keep the user from touching RF device 52 during use which can cause erroneous force readings.

A memory 54 can be included with RF device 52. Memory 54 can be an EPROM and the like. Additionally, a second non-volatile memory can be included in handpiece housing 12 for purposes of storing handpiece 10 information such as but not limited to, handpiece model number or version, handpiece software version, number of RF applications that handpiece 10 has delivered, expiration date and manufacture date. Handpiece housing 12 can also contain a microprocessor 58 for purposes of acquiring and analyzing data from various sensors on handpiece housing 12 or RF device 52 including but not limited to thermal sensors 42, force sensors 44, fluid pressure gauges, switches, buttons and the like.

Microprocessor 58 can also control components on handpiece 10 including but not limited to lights, LEDs, valves, pumps or other electronic components. Microprocessor 58 can also communicate data to a microprocessor of the RF generator.

Memory 54 can be utilized to assist in a variety of different functions including but not limited to, (i) controlling an amount of current delivered by RF electrode 20, (ii) controlling energy delivery duration time of RF electrode 20, (iii) controlling a temperature of RF electrode 20 relative to a target temperature, (iv) providing a maximum number of firings of RF electrode 20, (v) providing a maximum allowed voltage that is deliverable by RF electrode 20, (vi) a history of RF electrode 20 use, (vii) a controllable duty cycle to fluid delivery member 22, (viii) providing a controllable delivery rate of cooling media delivered from fluid delivery member 22, (ix) providing an amount of time that RF electrode 20 can be used, (x) providing an amount of RF electrode 20 usage, (xi) providing a number of areas treated by RF electrode 20, (xii) providing a number of times RF electrode 20 has been moved relative to the skin surface, (xiii) providing time or date of RF electrode 20 usage, (xiv) providing a thickness of the stratum corneum, (xv) providing an amount of energy delivered by RF electrode 20, (xvi) providing a status of RF electrode 20, (xvii) providing a status of RF generator, (xviii) providing information relative to a change of tissue in response to energy delivered by RF electrode 20, (xix) providing status information of fluid delivery member 22, (xx) providing temperature information relative to fluid delivery member, (xxi) providing temperature information relative to thermo-electric cooler 23, and the like.

Figure 5:
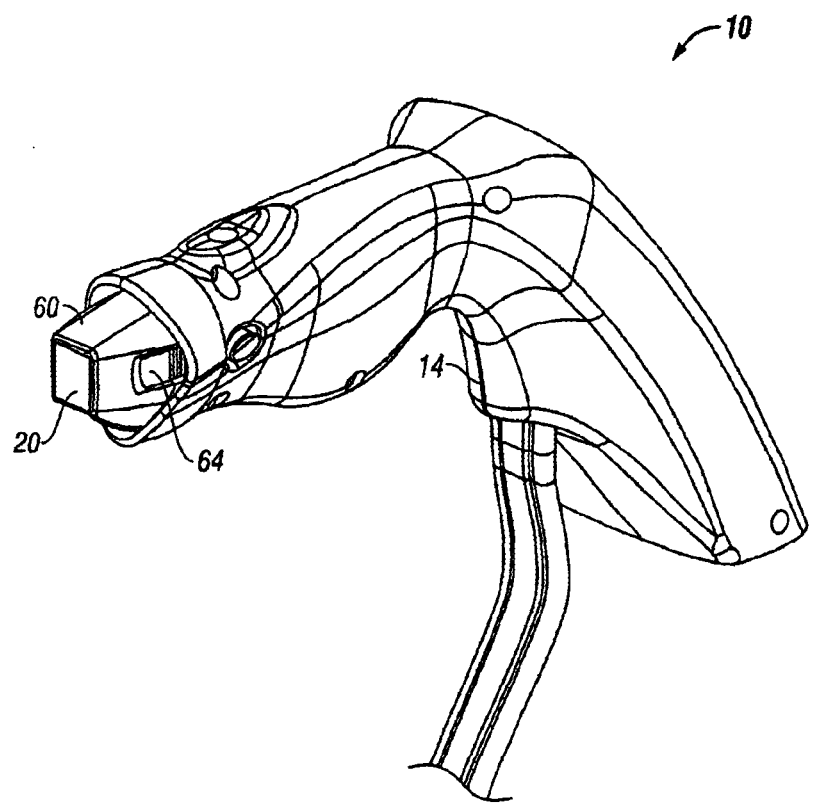
FIG. 5 is a side view of one embodiment of an RF handpiece assembly of the present invention.
Figure 6:
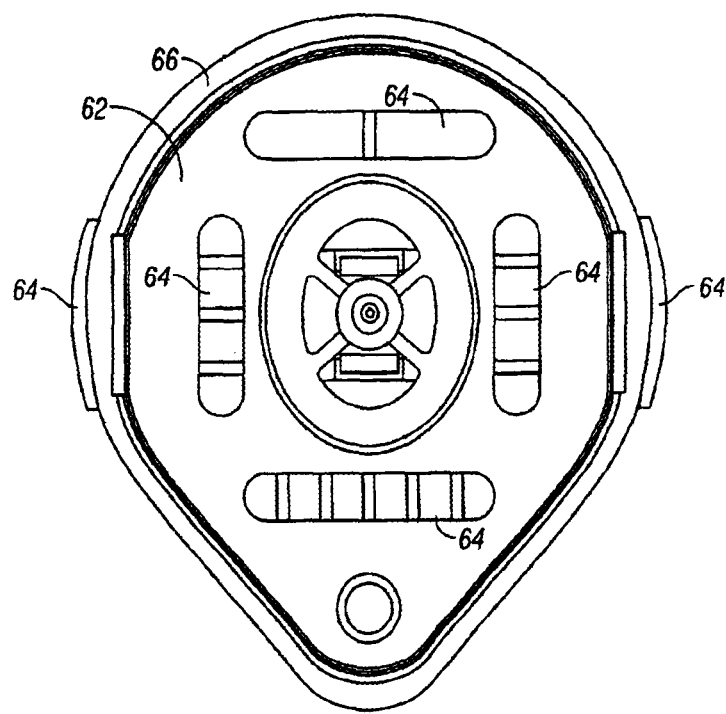
FIG. 6 is a rear view of the FIG. 5 RF electrode assembly.
Figure 7:
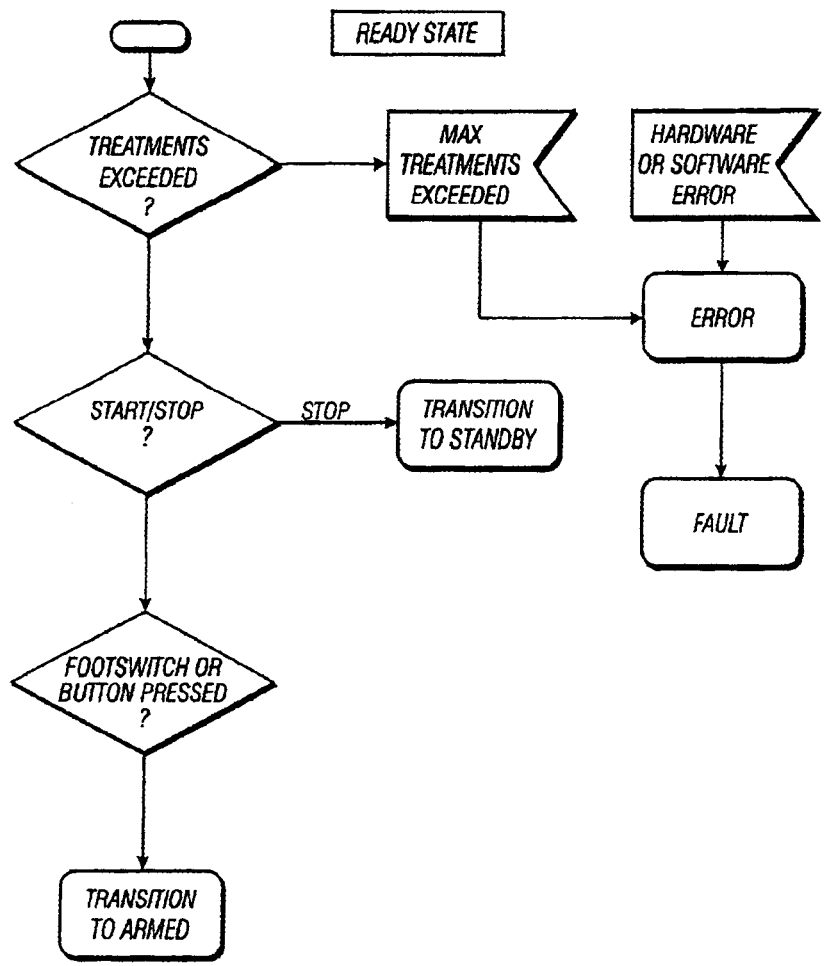
Figure 8:
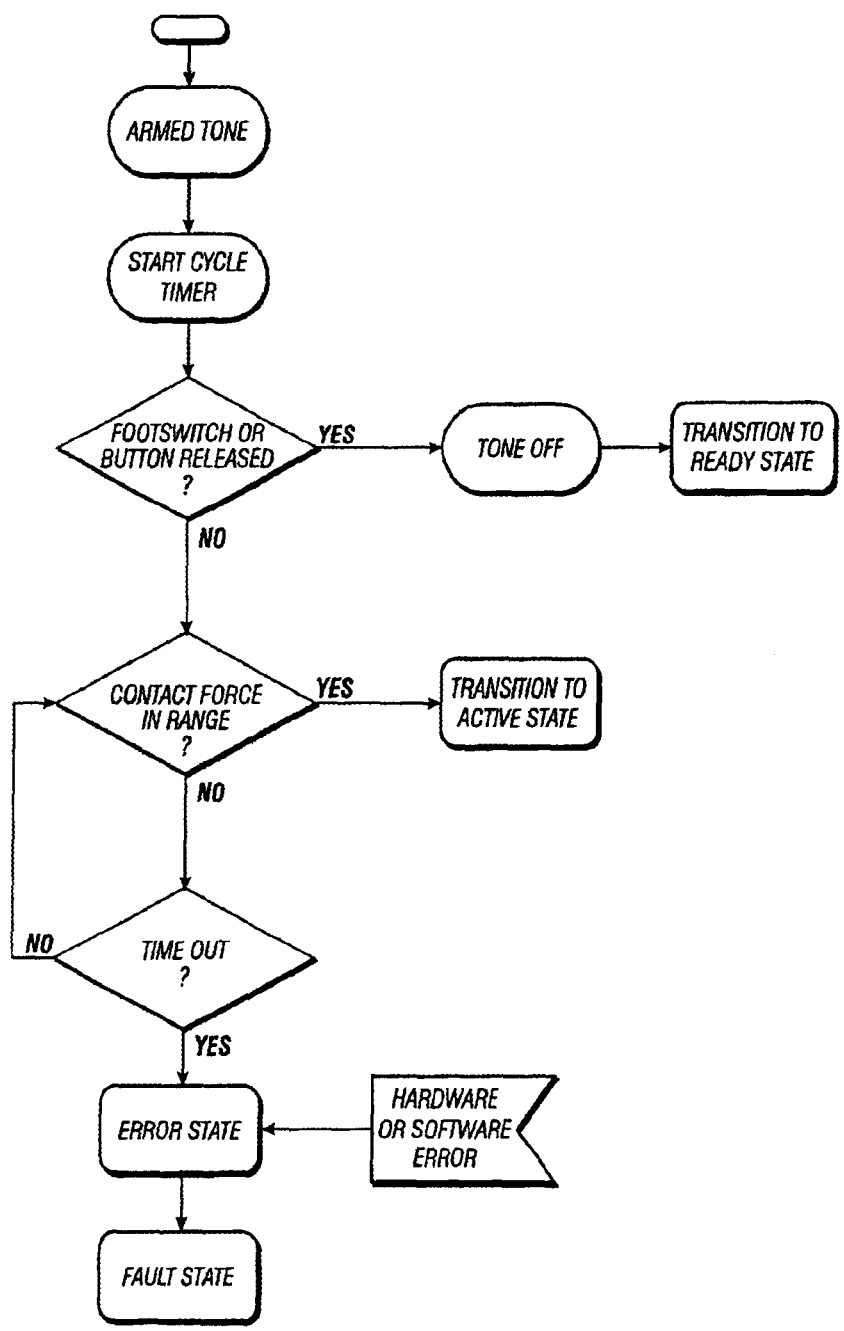
Figure 9:
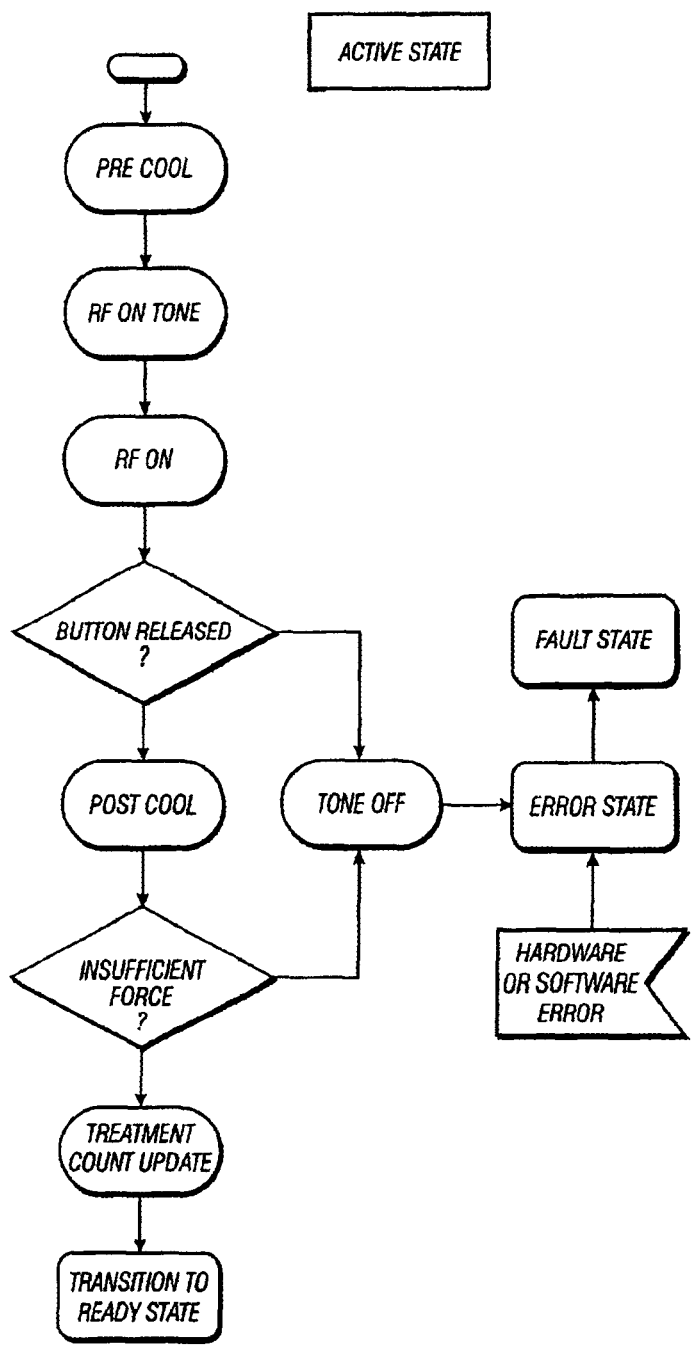
Figure 10:
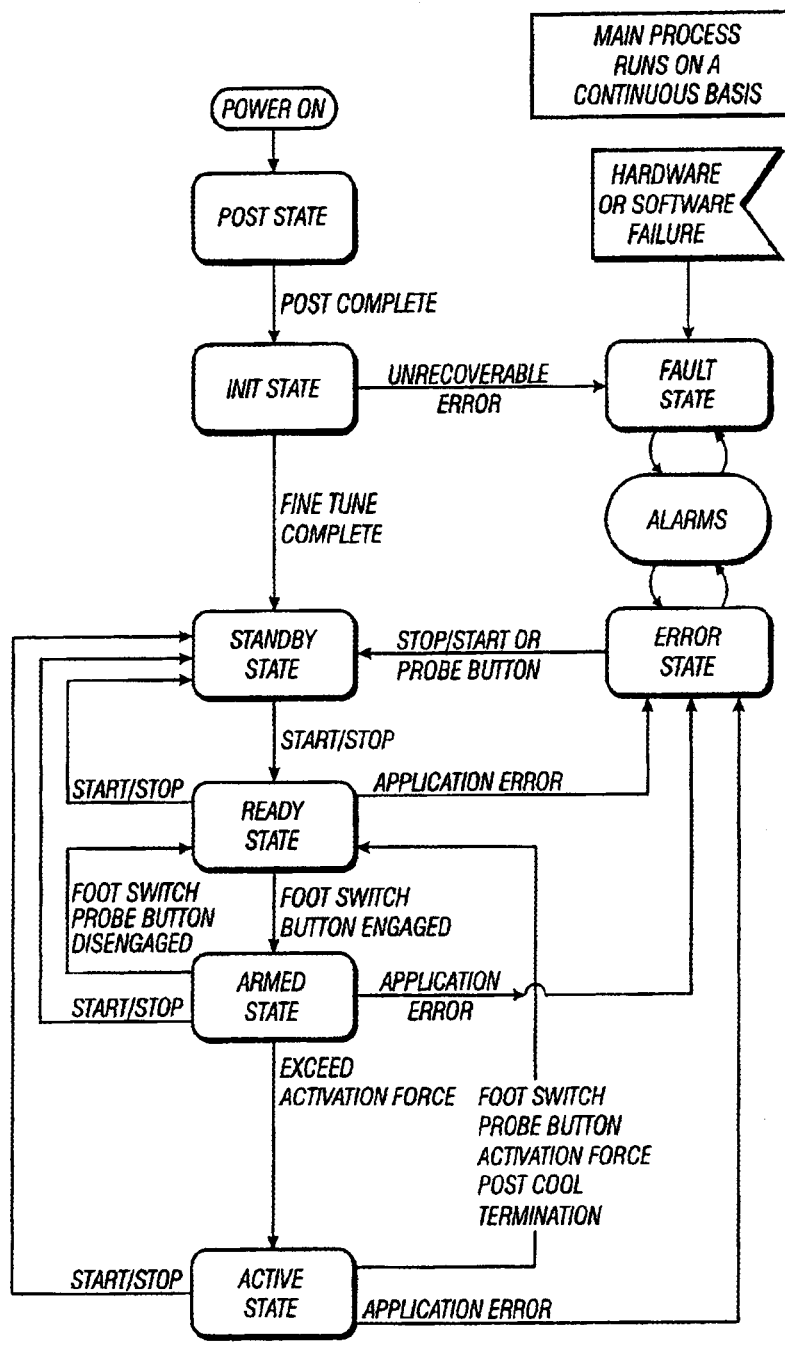
Figure 11:
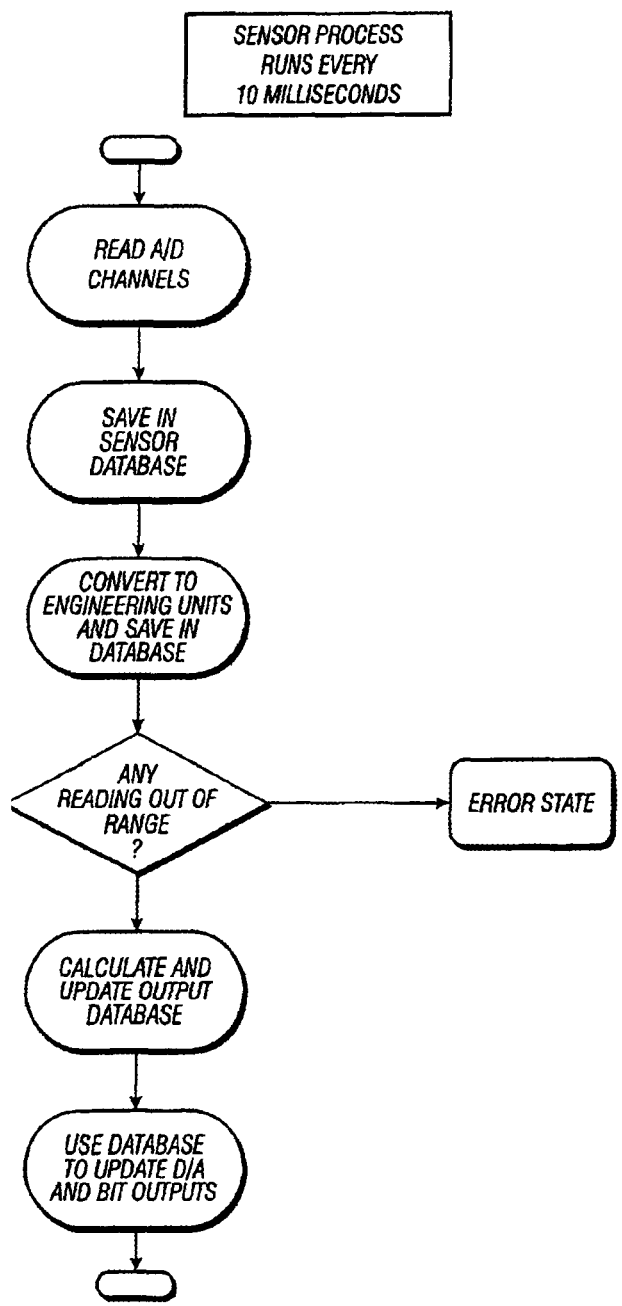
Figure 12:
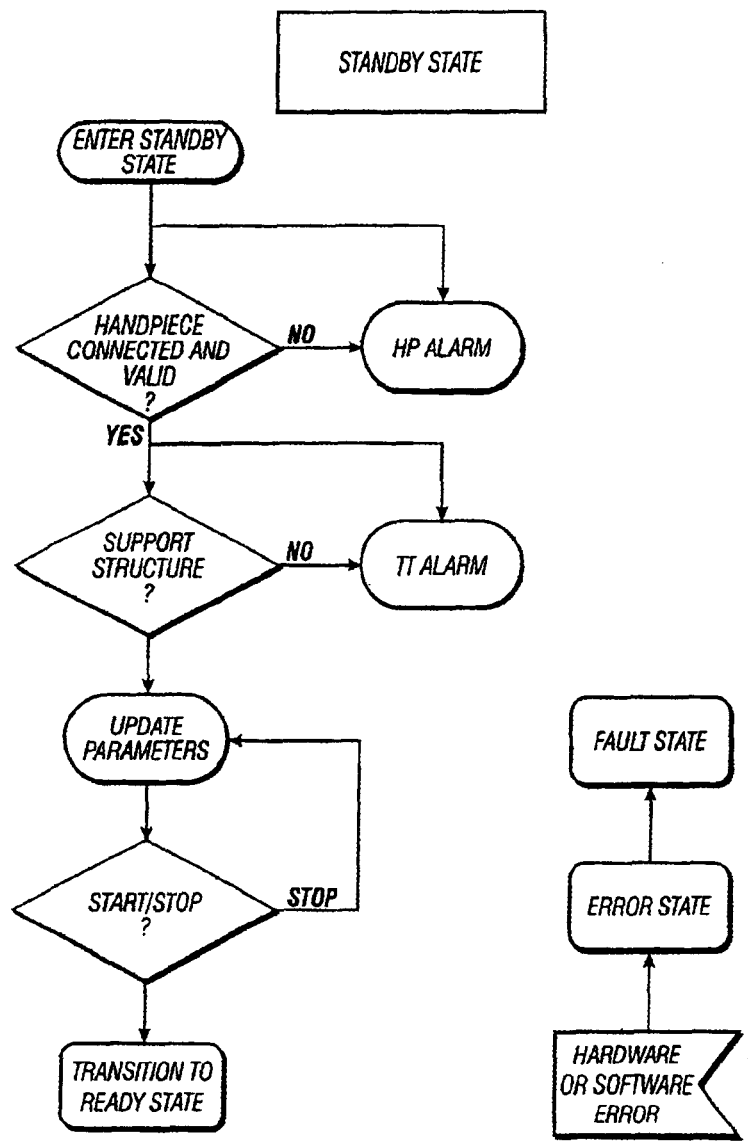
Figure 13:
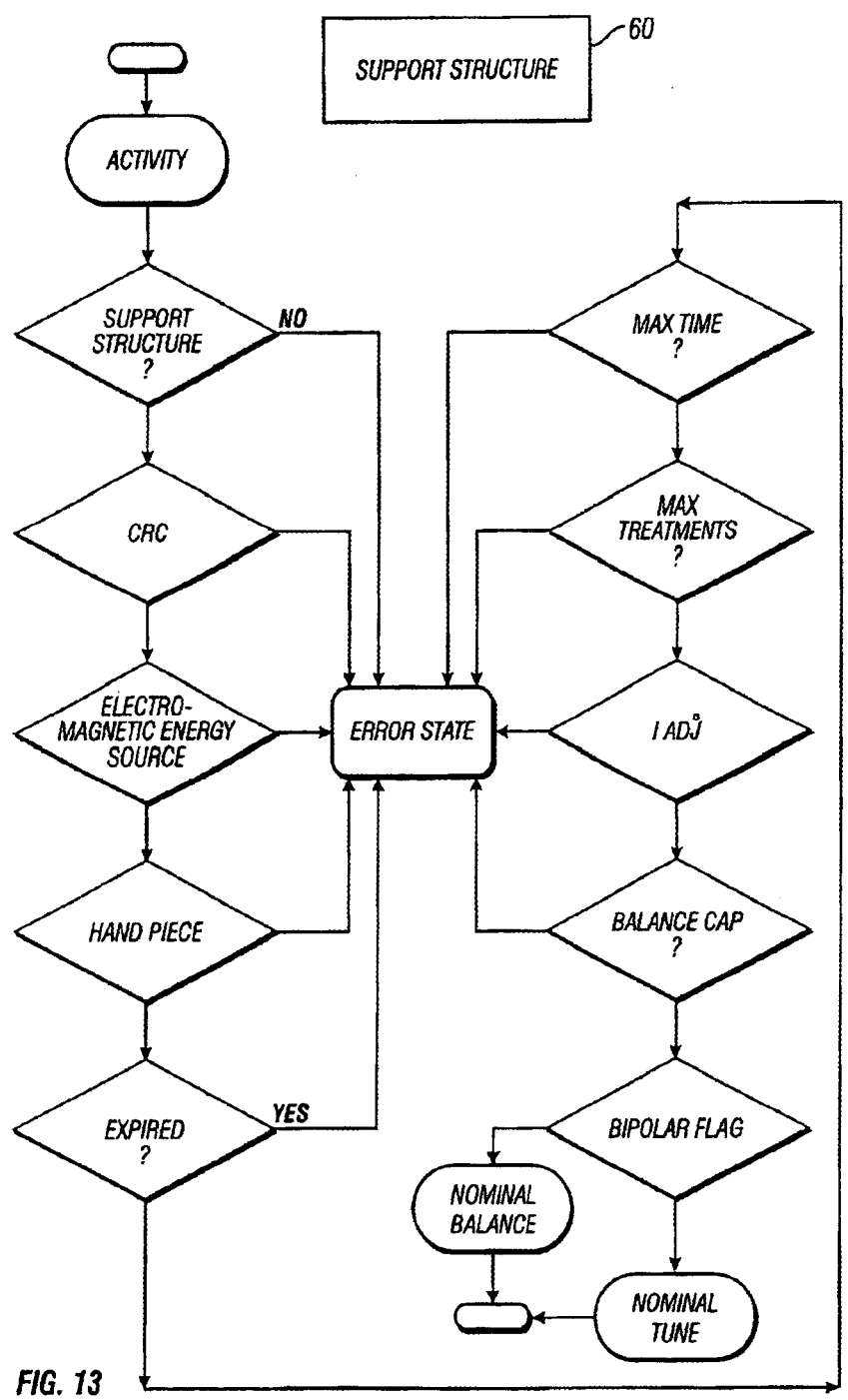

Referring now to FIGS. 5 and 6, RF device 52 includes a support structure 60, including but not limited to a housing 60 that defines the body of RF device 52. RF device 52 can include a back plate 62 that is positioned at a proximal portion of support structure 60. A plurality of electrical contact pads 64 can be positioned at back plate 62. At least a portion of fluid delivery member 22 and thermo-electric cooler 23 can extend through back plate 62. Fluid delivery member 22 can be a channel with a proximal end that is raised above the back surface of back plate 62.

First and second engagement members 64 can also be formed in the body of support structure 60. Engagement members 64 provide engagement and disengagement with handpiece housing 14. Suitable engagement members 64 include but are not limited to snap members, apertures to engage with snap members of support structure 60, and the like.

Handpiece 10 can be used to deliver thermal energy to modify tissue including, but not limited to, collagen containing tissue, in the epidermal, dermal and subcutaneous tissue layers, including adipose tissue. The modification of the tissue includes modifying a physical feature of the tissue, a structure of the tissue or a physical property of the tissue. The modification can be achieved by delivering sufficient energy to modify collagen containing tissue, cause collagen shrinkage, and/or a wound healing response including the deposition of new or nascent collagen, and the like.

Handpiece 10 can be utilized for performing a number of treatments of the skin and underlying tissue including but not limited to, (i) dermal remodeling and tightening, (ii) wrinkle reduction, (iii) elastosis reduction, (iv) scar reduction, (v) sebaceous gland removal/deactivation and reduction of activity of sebaceous gland, (vi) hair follicle removal, (vii) adipose tissue remodeling/removal, (viii) spider vein removal, (ix) modify contour irregularities of a skin surface, (x) create scar or nascent collagen, (xi) reduction of bacteria activity of skin, (xii) reduction of skin pore size, (xiii) unclog skin pores and the like.

In various embodiments, handpiece 10 can be utilized in a variety of treatment processes, including but not limited to, (i) pre-cooling, before the delivery of energy to the tissue has begun, (ii) an on phase or energy delivery phase in conjunction with cooling and (iii) post cooling after the delivery of energy to tissue has stopped. Thus, in various embodiments, cooling can be delivered at different rates, e.g., during treatment phases, before, during and after delivery of the energy to the tissue site.

In one embodiment, at least a portion of the tissue site is photographed before the tissue site treatment by the System under a first set of conditions. At some time after the tissue site treatment is completed, at least a portion of the treatment site is photographed under substantially the same conditions as those of the first set of conditions.

Handpiece 10 can be used to pre-cool the surface layers of the target tissue so that when RF electrode 20 is in contact with the tissue, or prior to turning on the RF energy source, the superficial layers of the target tissue are already cooled. When RF energy source is turned on or delivery of RF to the tissue otherwise begins, resulting in heating of the tissues, the tissue that has been cooled is protected from thermal effects including thermal damage. The tissue that has not been cooled will warm up to therapeutic temperatures resulting in the desired therapeutic effect.

Pre-cooling gives time for the thermal effects of cooling to propagate down into the tissue. More specifically, pre-cooling allows the achievement of a desired tissue depth thermal profile, with a minimum desired temperature being achieved at a selectable depth. The amount or duration of pre-cooling can be used to select the depth of the protected zone of untreated tissue. Longer durations of pre-cooling produce a deeper protected zone and hence a deeper level in tissue for the start of the treatment zone. The opposite is true for shorter periods of pre-cooling. The temperature of front surface 26 of RF electrode 20 also affects the temperature profile. The colder the temperature of front surface 26, the faster and deeper the cooling, and vice verse.

Post-cooling can be important because it prevents and/or reduces heat delivered to the deeper layers from conducting upward and heating the more superficial layers possibly to therapeutic or damaging temperature range even though external energy delivery to the tissue has ceased. In order to prevent this and related thermal phenomena, it can be desirable to maintain cooling of the treatment surface for a period of time after application of the RF energy has ceased. In various embodiments, varying amounts of post cooling can be combined with real-time cooling and/or pre-cooling.

In various embodiments, handpiece 10 can be used in a varied number of pulse on-off type cooling sequences and algorithms may be employed. In one embodiment, the treatment algorithm provides for pre-cooling of the tissue by starting a spray of cryogenic cooling fluidic medium, followed by a short pulse of RF energy into the tissue. In this embodiment, the spray of cryogenic cooling fluidic medium continues while the RF energy is delivered, and is stopping shortly thereafter, e.g. on the order of milliseconds. This or another treatment sequence can be repeated again. Thus in various embodiments, the treatment sequence can include a pulsed sequence of cooling on, heat, cooling off, cooling on, heat, cool off, and with cooling and heating durations on orders of tens of milliseconds. In these embodiments, every time the surface of the tissue of the skin is cooled, heat is removed from the skin surface. Cryogenic cooling fluidic medium spray duration, and intervals between sprays, can be in the tens of milliseconds ranges, which allows surface cooling while still delivering the desired thermal effect into the deeper target tissue.

In various embodiments, the target tissue zone for therapy, also called therapeutic zone or thermal effect zone, can be at a tissue depth from approximately 100 $\mu$m beneath the surface of the skin down to as deep as 10 millimeters, depending upon the type of treatment. For treatments involving collagen contraction, it can be desirable to cool both the epidermis and the superficial layers of the dermis of the skin that lies beneath the epidermis, to a cooled depth range between 100 $\mu$m two millimeters. Different treatment algorithms can incorporate different amounts of pre-cooling, heating and post cooling phases in order to produce a desired tissue effect at a desired depth.

Various duty cycles, on and off times, of cooling and heating are utilized depending on the type of treatment. The cooling and heating duty cycles can be controlled and dynamically varied by an electronic control system known in the art. Specifically the control system can be used to control cooling fluidic medium valve member 16 and the RF power source.

Figure 7:
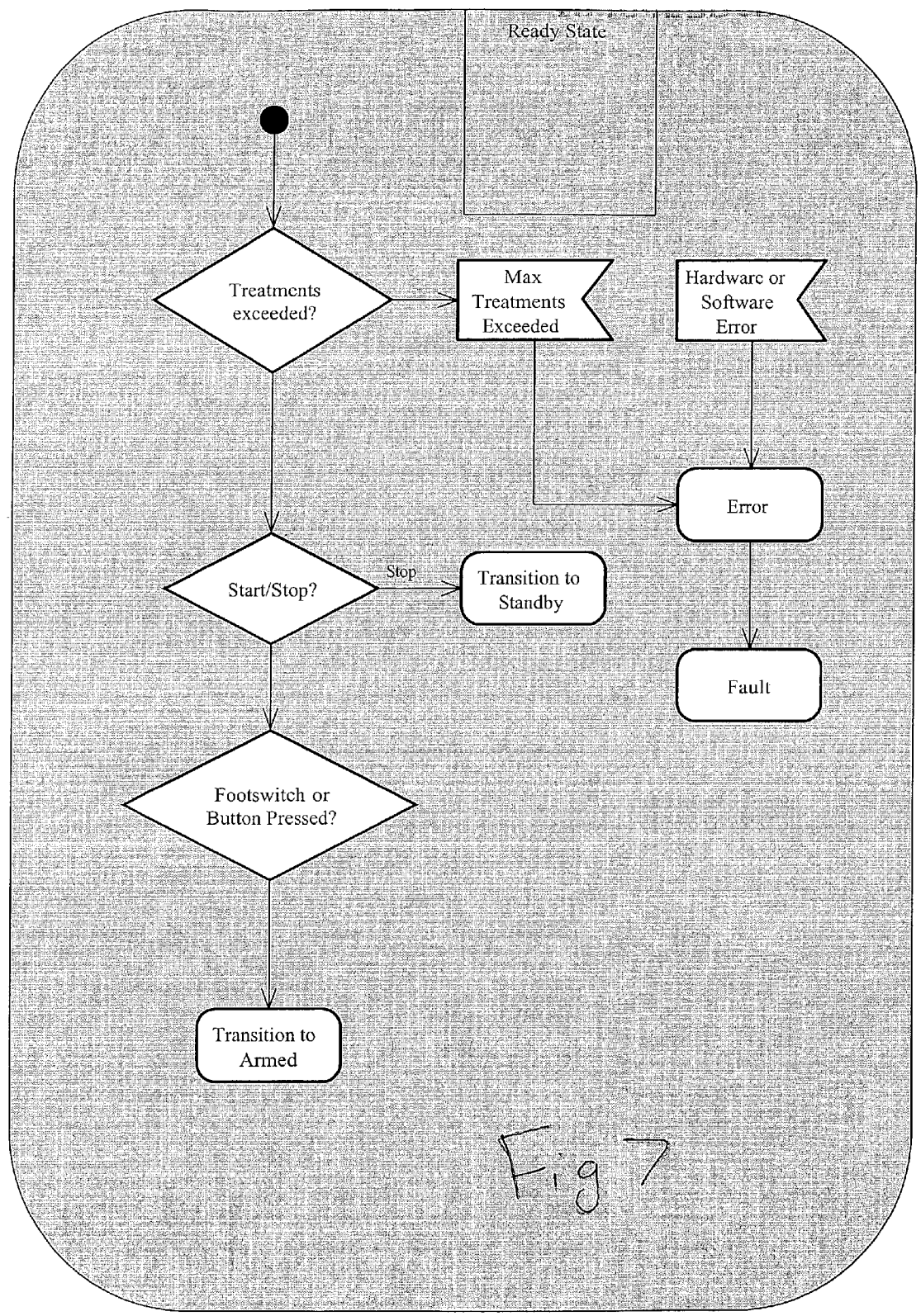
FIG. 7 is a flow chart that illustrates one embodiment of a ready state of a handpiece and its associated electromagnetic energy source (the "System").

In one embodiment, handpiece 10 is utilized in a variety of different states, including but not limited to, ready, armed, active, standby and the like. The ready state is illustrated in FIG. 7, where in one embodiment memory 54 is checked to see in the maximum treatment and/or the maximum number of treatments has been exceeded. If so, then there is an error state and a signal is provide to the physician. If neither one has been exceeded, and activation button 46 has not been pressed, then there is a wait until activation button 46, or an associated footswitch, is activated. It either one is activated, then the System proceeds to the armed state.

Figure 8:
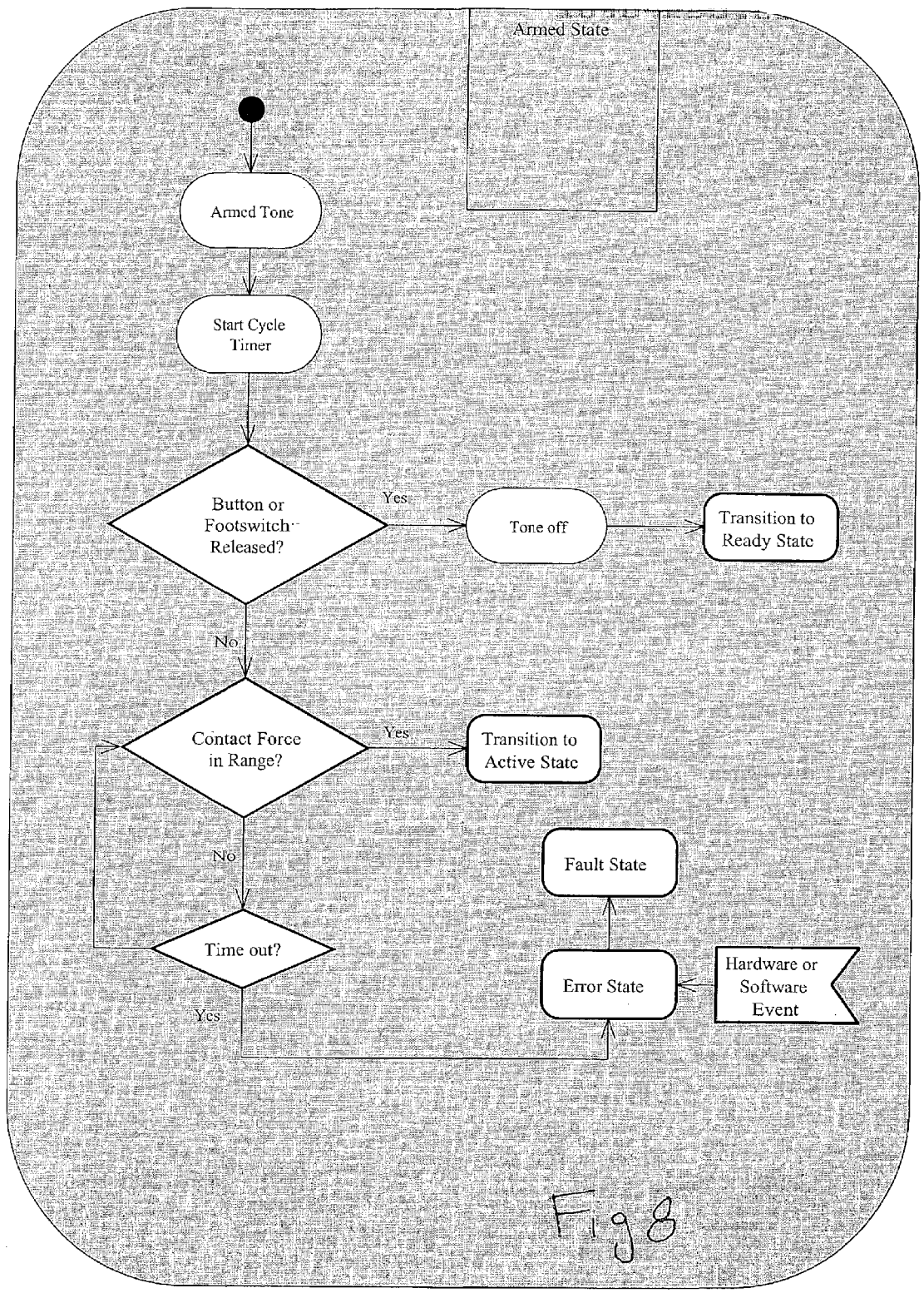
FIG. 8 is a flow chart that illustrates one embodiment of an armed state of the System.

In the armed state, shown in FIG. 8, an armed tone can be provided, and in one embodiment three seconds are allowed for the physician to cause handpiece 10 to become coupled to a skin surface, which can be direct physical contact with the skin surface of the patient. If more than the allotted time has passed, then the System is in an error state. Force sensor 44 is used to determine when there is contact by handpiece 10 with the patient. If there is the proper amount of force applied by handpiece 10, then there is a transition to the active state.

Figure 9:
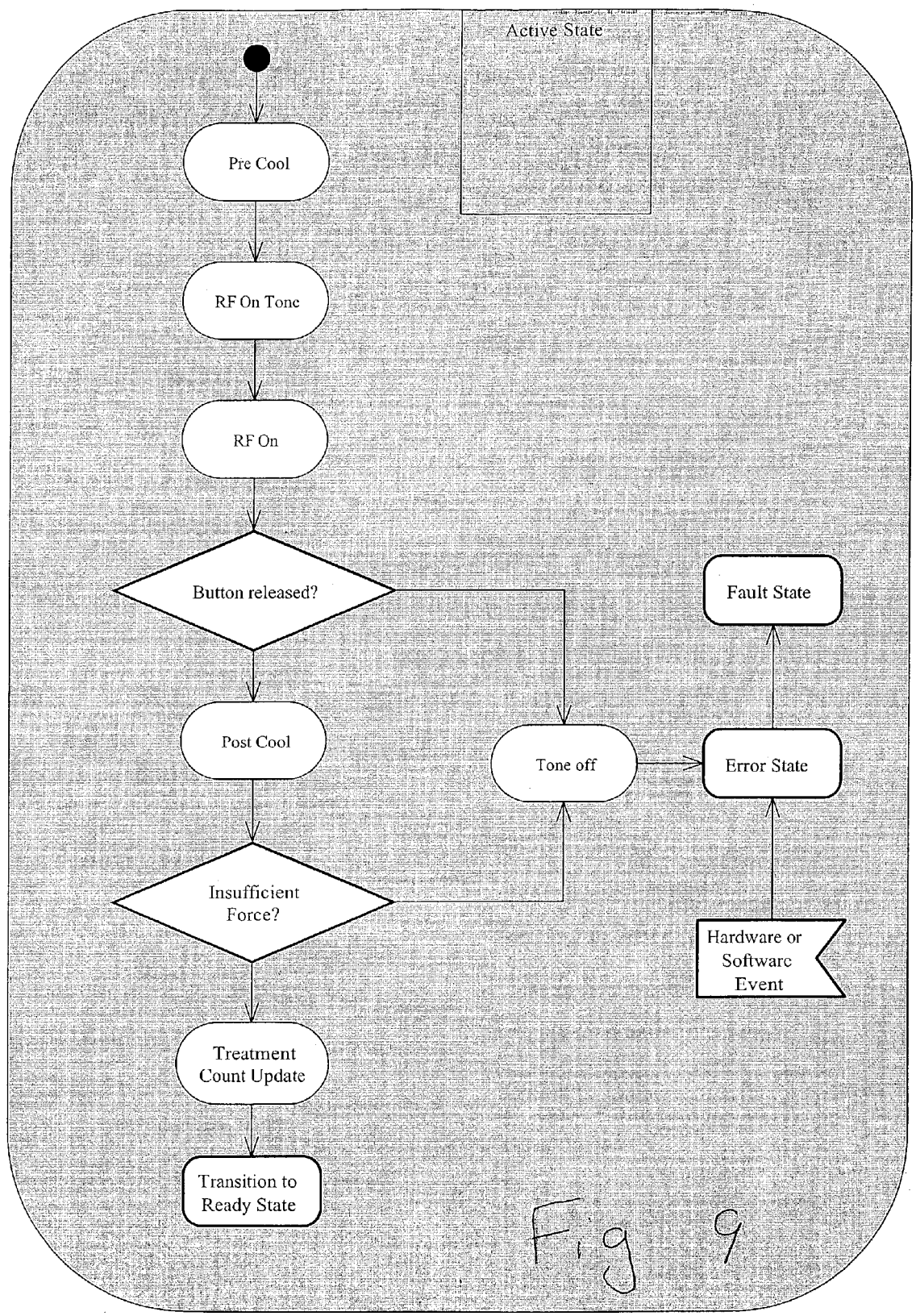
FIG. 9 is a flow chart that illustrates one embodiment of an active state of the System.

As illustrated in FIG. 9, the active begins when there is actual contact by handpiece 10 with the patient. A pre-cool is first applied to the skin surface. Electromagnetic energy, such as RF, is then delivered. If activation button 46 is released a tone or other indicator can go off and the System is again in an error state. This can occur at any time. Following delivery of electromagnetic energy, there is a post cooling state. The levels of cooling delivered to the skin surface at pre-cooling, during electromagnetic energy delivery, and post-cooling, can each be different.

Figure 10:
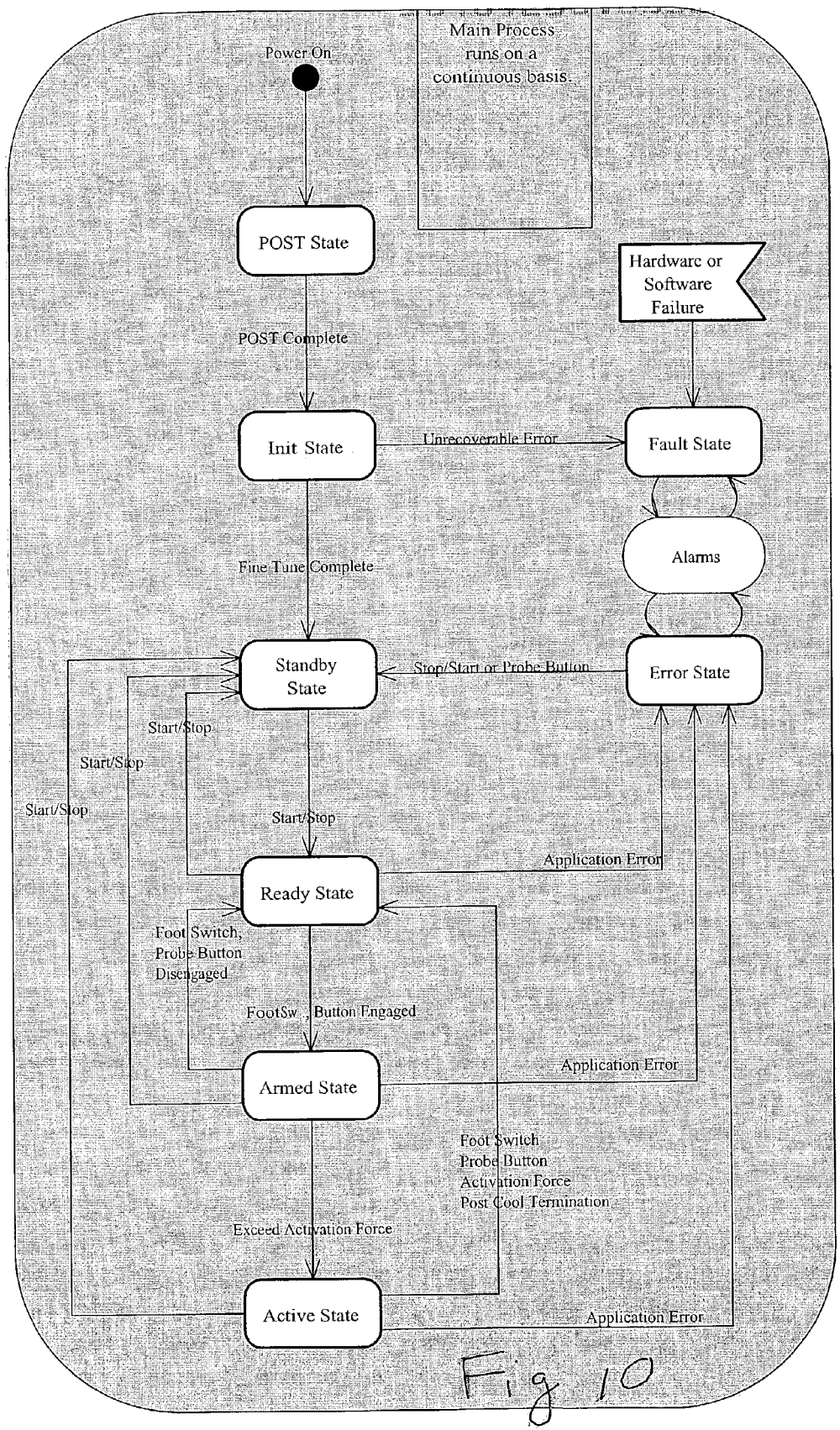
FIG. 10 is a flow chart that illustrates one embodiment of a main control loop that can be utilized with the present invention.

FIG. 10 illustrates an embodiment where a main control loop is provided that self tests the System. Following the self test, there is an initialization of the System, followed by a fine tuning, and then the System is prepared for the ready state.

Figure 11:
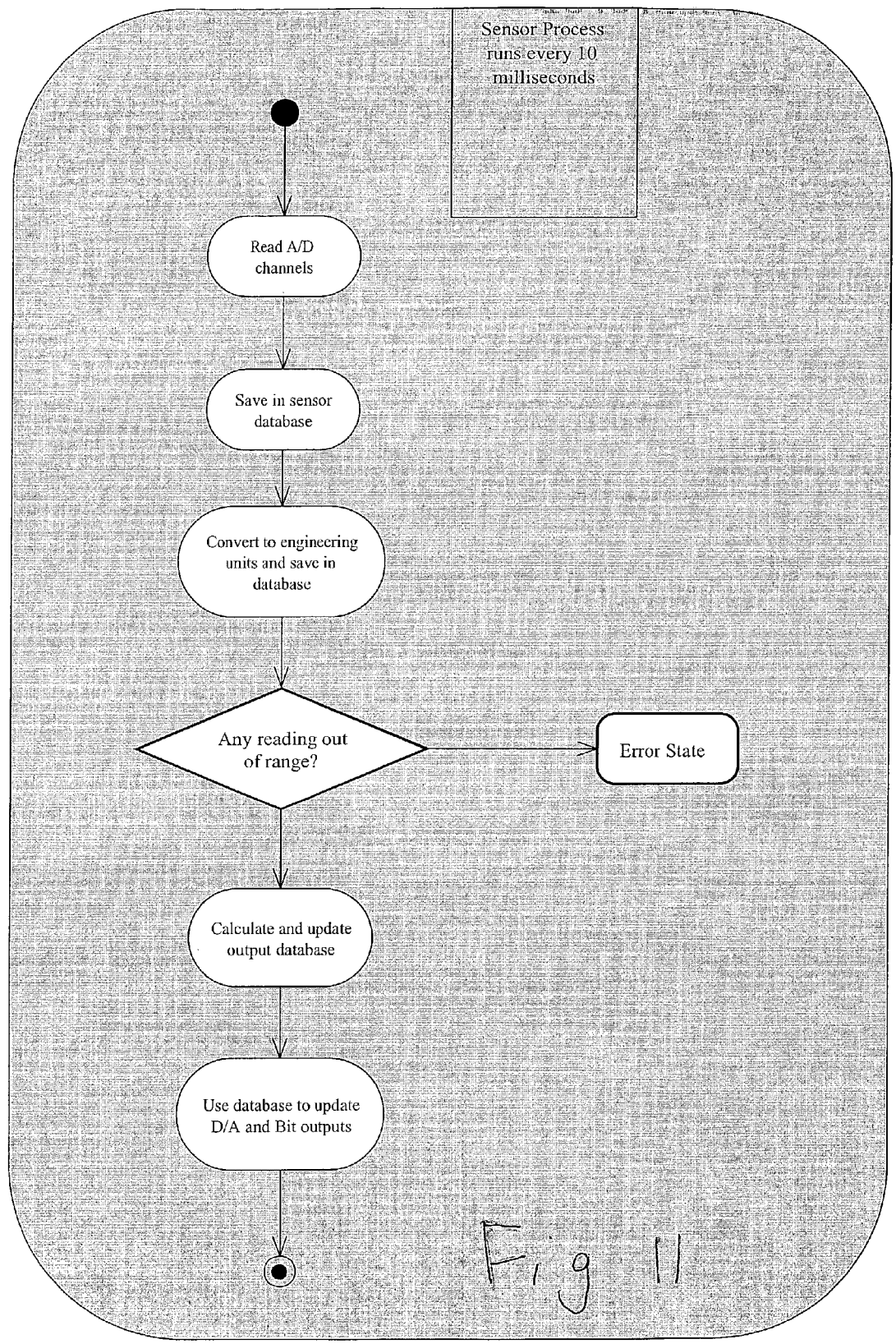
FIG. 11 is a flow chart that illustrates how the System of the present invention can check the channels of the associated sensors utilized with the present invention.
Figure 12:
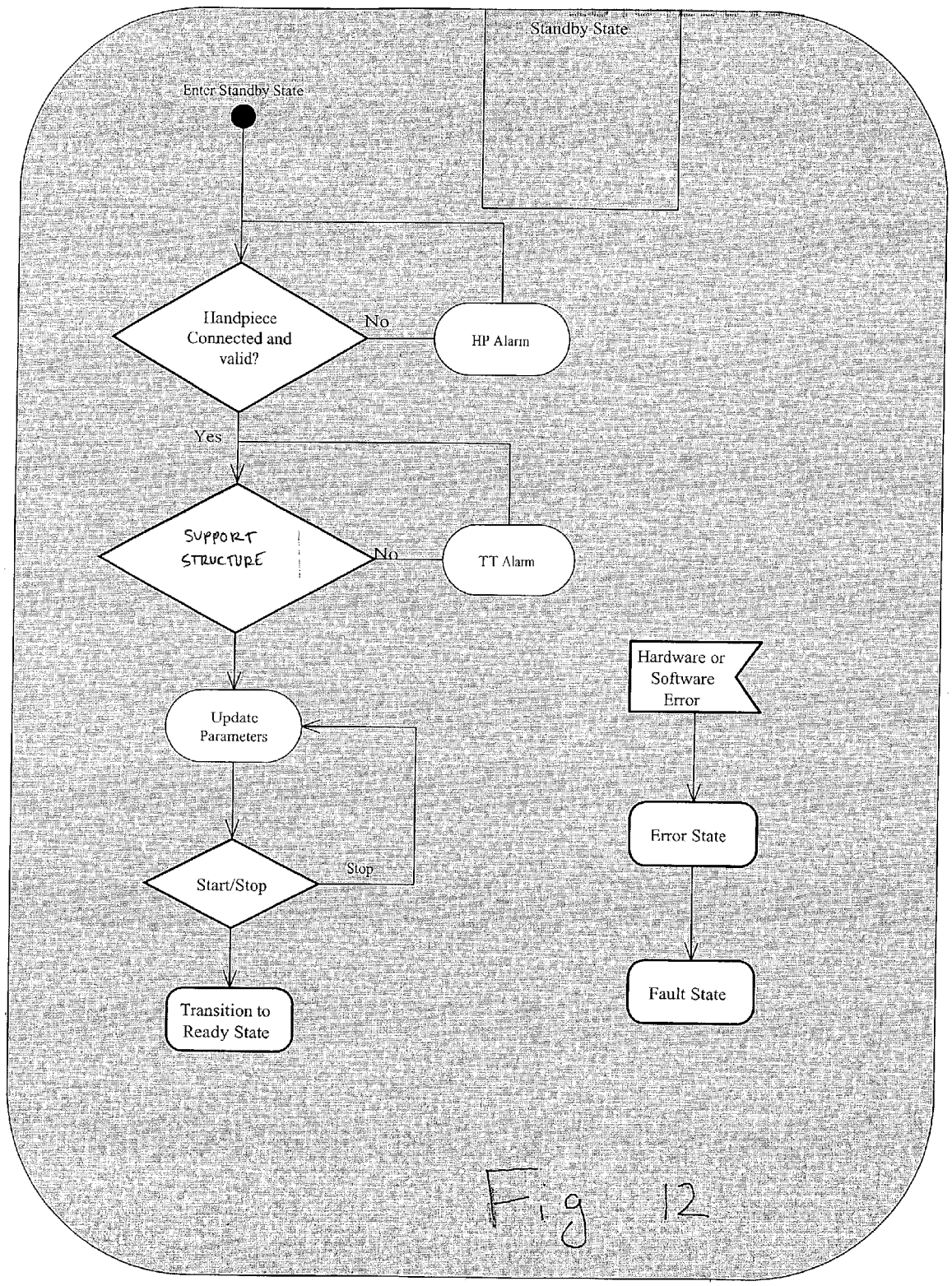
FIG. 12 is a flow chart that illustrates one embodiment of an active state of the System.

As illustrated in FIG. 11, all channels from the sensors, including but not limited to voltage, current power, temperature, and the like, are read. An updated set of current values is created. Checks are then made, as illustrated in FIG. 12, to make sure that handpiece 10 is connected to the electromagnetic energy source, and that the particular handpiece 10 is a valid one suitable for use with the electromagnetic energy source. A check is also made that support structure 60 is connected and also valid, e.g., that the support structure 60 is a suitable for use with handpiece 10 and the electromagnetic energy source. The parameters of a treatment tip associated with support structure are then updated, followed by transition to the ready state when activation button 46 or the footswitch is depressed.

Figure 13:
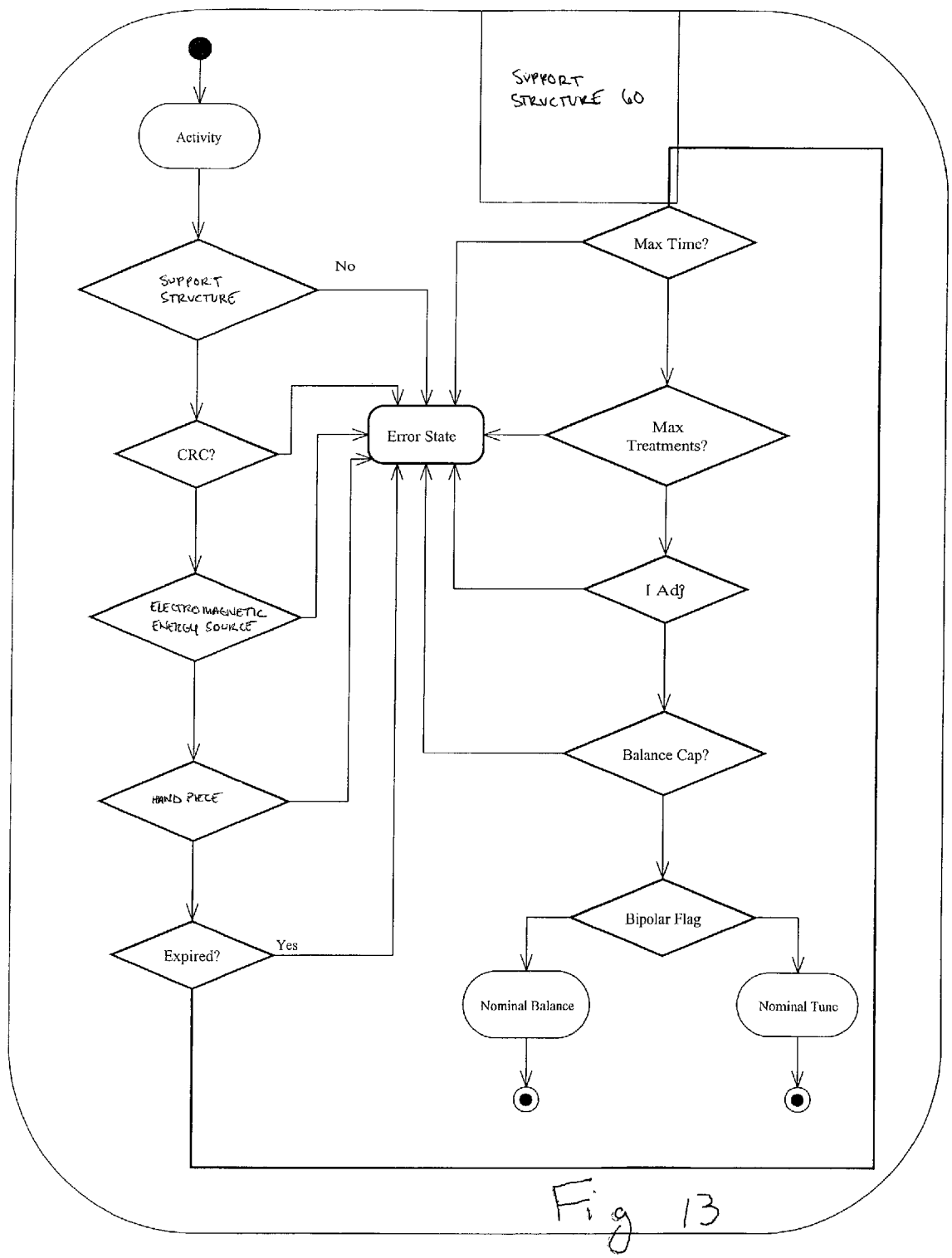
FIG. 13 is a flow chart that illustrates one embodiment of checking a support structure of the present invention.
Figure 1A:
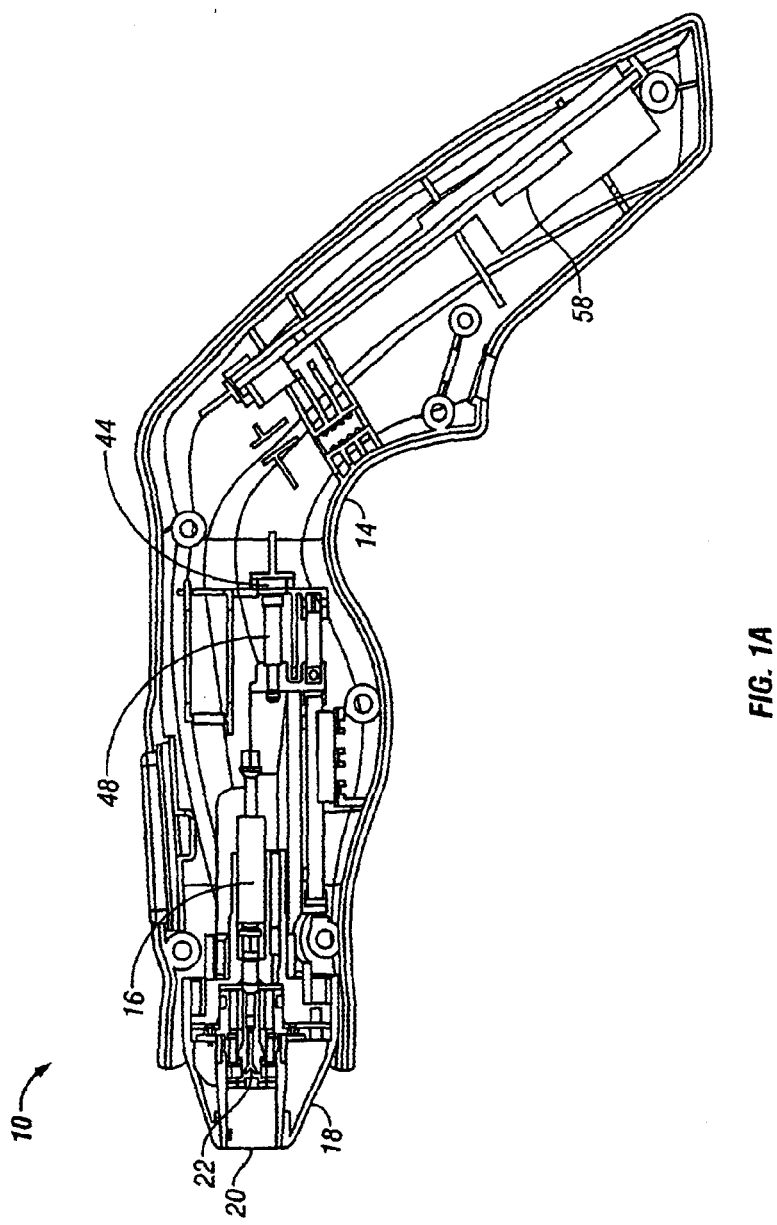
Figure 2:
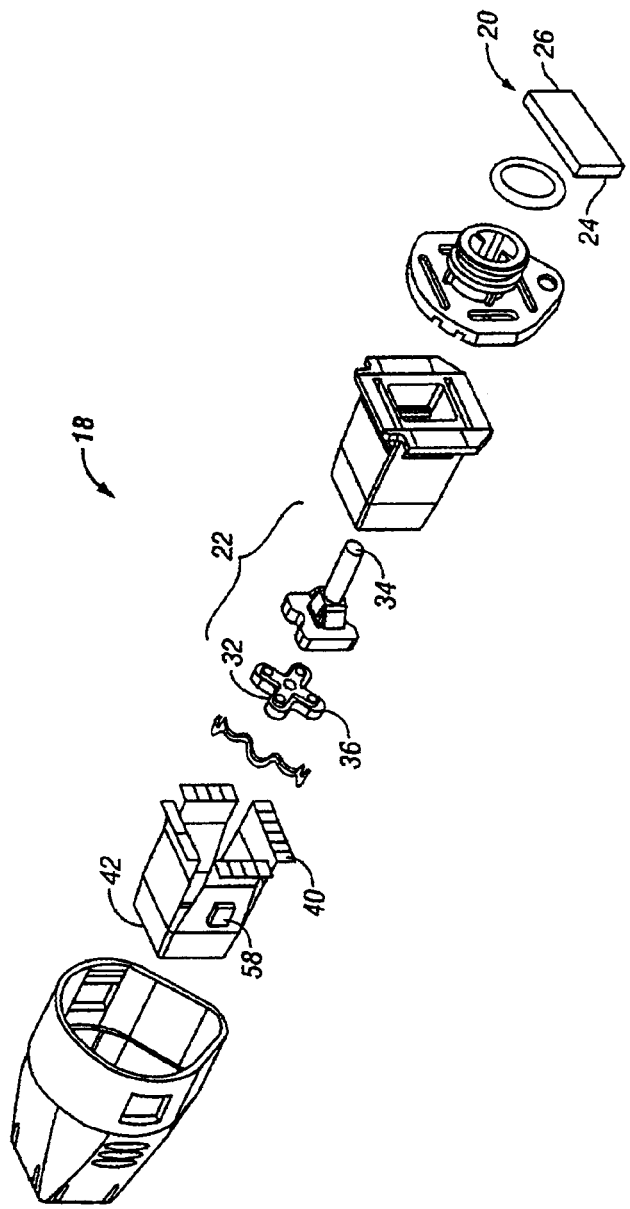
Figure 1B:
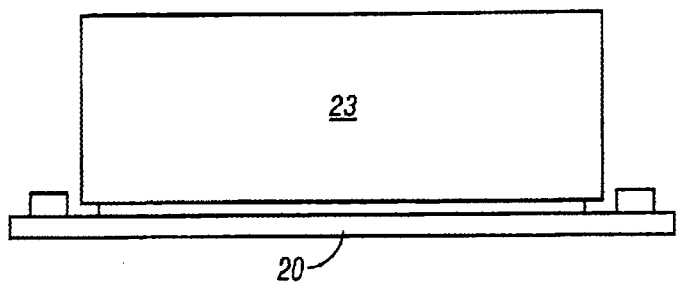

Referring now to FIG. 13, support structure is checked to make sure that it is connected. The CRC of a memory code of memory 54 is also checked. Checks are also made to make sure that the electromagnetic energy source, and handpiece 10 are acceptable devices. If there is expiration of any of the devices, including but not limited to support structure 60, or a device is not acceptable, the System is in an error state.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

The invention claimed is:

1. An apparatus for treating skin tissue, comprising:
   an electromagnetic energy delivery device configured to be coupled to an electromagnetic energy source, the device including an electrode with a tissue contacting portion, the electrode configured to produce a tissue effect on the skin tissue;
   a non-ambient cooling member configured to create a reverse thermal gradient through an outer layer of the skin tissue to an underlying tissue;
   a plurality of sensors coupled to the electrode; and
   a control operatively coupled to the sensors and configured to determine whether at least a portion of the tissue contacting portion of the electrode is out of contact with the skin.

2. The apparatus of claim 1, wherein each sensor is a thermal sensor.

3. The apparatus of claim 2, wherein each sensor is selected from a thermocouple, thermistor, infrared photo-emitter or a thermally sensitive diode.

4. The apparatus of claim 1, wherein the electromagnetic energy source is an RF source.

5. The apparatus of claim 1, wherein the electromagnetic energy delivery device is an RF electrode and a memory is utilized to assist in controlling an amount of current delivered by the RF electrode.

6. The apparatus of claim 1, wherein the electromagnetic energy delivery device is an RF electrode and a memory is utilized to assist in providing a maximum allowed voltage that is deliverable by the RF electrode.

7. The apparatus of claim 1, wherein a memory is utilized to assist in controlling energy delivery duration time of the electromagnetic energy delivery device.

8. The apparatus of claim 1, wherein a memory is utilized to assist in controlling a temperature of the electromagnetic energy delivery device relative to a target temperature.

9. The apparatus of claim 1, wherein a memory is utilized to assist in providing a maximum number of firings of the electromagnetic energy delivery device.

10. The apparatus of claim 1, wherein a memory is utilized to assist in providing a history of energy delivery device use.

11. The apparatus of claim 1, wherein a memory is utilized to assist in providing a controllable duty cycle to the non-ambient cooling member.

12. The apparatus of claim 1, wherein a memory is utilized to assist in providing a controllable delivery rate of cooling delivered from the non-ambient cooling member.

13. The apparatus of claim 1, wherein a memory is utilized to assist in providing an amount of time that the electromagnetic energy delivery device can be used.

14. The apparatus of claim 1, wherein a memory is utilized to assist in providing an amount of energy delivery device usage.

15. The apparatus of claim 1, wherein a memory is utilized to assist in providing a number of areas treated by the electromagnetic energy delivery device.

16. The apparatus of claim 1, wherein a memory is utilized to assist in providing a number of times the electromagnetic energy delivery device has been moved relative to the skin surface.

17. The apparatus of claim 1, wherein a memory is utilized to assist in providing at least one of time or date of electromagnetic energy delivery device usage.

18. The apparatus of claim 1, wherein a memory is utilized to assist in providing an amount of energy delivered by the electromagnetic energy delivery device.

19. The apparatus of claim 1, wherein a memory is utilized to assist in providing a status of the electromagnetic energy delivery device.

20. The apparatus of claim 1, wherein a memory is utilized to assist in providing a status of the electromagnetic energy source.

21. The apparatus of claim 1, wherein a memory is utilized to assist in providing information relative to a change of tissue in response to energy delivered by the electromagnetic energy delivery device.

22. The apparatus of claim 1, wherein the electrode includes a dielectric portion.

23. An apparatus for treating skin tissue comprising:
   an electromagnetic energy source;
   an electromagnetic energy delivery device coupled to the electromagnetic energy source, the device including an electrode with a tissue contacting portion, the electrode configured to produce a tissue effect on the skin tissue;
   a non-ambient cooling member configured to create a reverse thermal gradient through an outer layer of the skin tissue to an underlying tissue;

a plurality of sensors coupled to the electrode; and a control operatively coupled to the sensors and configured to determine whether at least a portion of the tissue contacting portion of the electrode is out of contact with the skin.

24. The apparatus of claim 23, wherein the electrode includes a dielectric portion.

25. A method of producing a tissue effect with an electromagnetic energy delivery device including an electrode with a tissue contacting portion and a plurality of sensors operatively coupled with the tissue contacting portion, the method comprising:

contacting the skin of a patient with the tissue contacting portion;

delivering electromagnetic energy through the skin with the electrode; and using the sensors to detect whether the tissue contacting portion is out of complete contact with the skin of the patient.

26. The method of claim 25, further comprising:

using the sensors to detect whether the tissue contacting portion is only partially contacting the skin of the patient.

* * * * *

UNITED STATES PATENT AND TRADEMARK OFFICE
CERTIFICATE OF CORRECTION

PATENT NO. : 7,006,874 B2
APPLICATION NO. : 10/404250
DATED : February 28, 2006
INVENTOR(S) : Knowlton et al.

It is certified that error appears in the above-identified patent and that said Letters Patent is hereby corrected as shown below:

In the Title Pages (56):

Page 3, column 1, "Tucek et al." should read --Shanks et al.--.

Page 5, column 1, "Acsthetics" should read --Aesthetics--.

Page 5, list the following publications:

--Syneron Medical, Ltd., Syneron, Inc., "Motion for Leave to File Syneron's Surreply in Opposition to Preliminary Injunction Motion," September 10, 2004.

Syneron Medical, Ltd., Syneron, Inc., "Surreply in Opposition to Thermage, Inc.'s Preliminary Injunction Motion," September 10, 2004.

Syneron Medical, Ltd., Syneron, Inc., "Supplemental Declaration of Jill Neiman in Opposition to Preliminary Injunction Motion" and attached Exhibits A-C, September 10, 2004.

Syneron Medical, Ltd., Syneron, Inc., "Supplemental Declaration of Warren Grundfest in Opposition to Preliminary Injunction Motion" and attached Exhibits A-B, September 10, 2004.

Judge Charles R. Breyer, "Order granting Motion for Leave to File Surreply," September 13, 2004.

Thermage, Inc., "Memorandum in Opposition re Motion for Preliminary Injunction to Syneron's Surreply", September 14, 2004.

Judge Charles R. Breyer, "Order Regarding Questions for Oral Argument," September 16, 2004.

Thermage, Inc., "Answer to Counterclaim," September 16, 2004.

Thermage, Inc., "Minute Entry: Motion Hearing held on 9/17/2004 before Judge Charles R. Breyer re Motion for Preliminary Injunction," September 17, 2004.

Judge Charles R. Breyer, "Order denying Motion for Preliminary Injunction," September 27, 2004.

UNITED STATES PATENT AND TRADEMARK OFFICE
CERTIFICATE OF CORRECTION

| | | |
|---|---|---|
| PATENT NO. | : 7,006,874 B2 | |
| APPLICATION NO. | : 10/404250 | |
| DATED | : February 28, 2006 | |
| INVENTOR(S) | : Knowlton et al. | |

It is certified that error appears in the above-identified patent and that said Letters Patent is hereby corrected as shown below:

In the Title Pages (56) (con't):

Judge Charles R. Breyer, "Transcript of Proceedings held on 09/17/04," October 8, 2004.--

In The Specification:
  Column 2, line 63 insert --,-- after follicles;
  Column 3, line 23 "concentrate" should be changed to --concentrates--.
  Column 4, line 66 "the" should be changed to --The--.
  Column 5, line 15 and line 30, each occurrence of "reversal" should read --reverse--.
  Column 6, line 2 insert --of-- after area; line 3 delete "an" after illustrates.
  Column 7, line 12, insert --is-- after transition; line 35 delete "of" after because.
  Column 10, line 20, "If" should be changed to --It--; line 47, "fell" should be changed to --falls--.
  Column 13, line 62 "verse" should be changed to --versa--.
  Column 14, line 34 add --and-- before two; line 49 "in" should be changed to --if--; line 51 "provide" should be changed to --provided--.
Column 15, line 23 delete "a" before suitable.

In the Drawings:
The sheets of drawings consisting of Figures 1-13 should be deleted to appear as per attached figures 1-13.

Signed and Sealed this

Seventeenth Day of October, 2006

JON W. DUDAS
*Director of the United States Patent and Trademark Office*